(12) United States Patent
Aceros et al.

(10) Patent No.: US 12,178,764 B1
(45) Date of Patent: *Dec. 31, 2024

(54) MODULAR MEDICAL MOBILITY DEVICE

(71) Applicants: Juan Aceros, St. Johns, FL (US); Matthew Cantwell, Orange Park, FL (US); John Prisco, Holly Springs, GA (US)

(72) Inventors: Juan Aceros, St. Johns, FL (US); Matthew Cantwell, Orange Park, FL (US); John Prisco, Holly Springs, GA (US)

(73) Assignee: University of North Florida Board of Trustees, Jacksonville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/472,622

(22) Filed: Sep. 22, 2023

Related U.S. Application Data

(63) Continuation of application No. 17/247,346, filed on Dec. 8, 2020, now Pat. No. 11,786,418.

(60) Provisional application No. 62/945,656, filed on Dec. 9, 2019.

(51) Int. Cl.
| | |
|---|---|
| *A61G 5/10* | (2006.01) |
| *A61G 5/04* | (2013.01) |
| *A61M 16/00* | (2006.01) |
| *A61M 16/10* | (2006.01) |
| *B60D 1/01* | (2006.01) |
| *B60L 50/60* | (2019.01) |

(52) U.S. Cl.
CPC ............. *A61G 5/041* (2013.01); *A61G 5/10* (2013.01); *A61G 5/1056* (2013.01); *A61M 16/0003* (2014.02); *A61M 16/1005* (2014.02); *B60D 1/01* (2013.01); *B60L 50/60* (2019.02); *A61M 2209/082* (2013.01); *B60L 2200/24* (2013.01)

(58) Field of Classification Search
CPC .......... B62D 5/00; B62D 31/00; B62D 29/00; B62D 33/00; B62D 35/00; B62D 24/00; B62D 23/00; B60L 3/00; B60L 50/00; B60L 50/60; B60L 2200/24; A61G 5/041; A61G 5/10; A61G 5/1056; A61M 16/0003; A61M 16/1005; A61M 2209/082; B60D 1/01
USPC ........................................................ 180/268
See application file for complete search history.

(56) References Cited

U.S. PATENT DOCUMENTS

| | | | | |
|---|---|---|---|---|
| 2,587,142 A | * | 2/1952 | Gray .................... | B62D 29/046 446/94 |
| 2,803,920 A | * | 8/1957 | Salosky ................. | A63H 17/02 446/6 |

(Continued)

*Primary Examiner* — James A Shriver, II
*Assistant Examiner* — Hilary L Johns
(74) *Attorney, Agent, or Firm* — Owen G. Behrens; Smith & Hopen, P.A.

(57) ABSTRACT

A modular ride-on is provided that is adjustable based on the needs of the operator. The modular ride-on offers children and young adults with disabilities a higher degree of freedom and comfort over traditional mobility devices—such as wheelchairs. The modular ride-on includes a chassis configured to removably couple a plurality of adjustable modules. The independently adjustable modules include a front-end module, first and second drive modules, a seating module, a harness module, an armrest module, a footrest module, a leg support module, a body module, and a control module.

20 Claims, 50 Drawing Sheets

(56) References Cited

U.S. PATENT DOCUMENTS

| | | | | |
|---|---|---|---|---|
| 3,629,968 A * | 12/1971 | Linstead | A63H 17/002 | 446/95 |
| 3,811,218 A * | 5/1974 | Salmon | A63H 17/262 | 446/94 |
| 4,422,685 A * | 12/1983 | Bonfilio | B62D 65/04 | 296/193.04 |
| 4,842,326 A * | 6/1989 | DiVito | B60P 3/42 | 296/10 |
| 6,026,923 A * | 2/2000 | Uphaus | B60G 99/006 | 180/312 |
| 6,095,268 A * | 8/2000 | Jones, Jr. | B60L 15/007 | 180/65.6 |
| 7,059,661 B2 * | 6/2006 | Mataja | B62K 9/00 | 446/470 |
| 7,100,968 B2 * | 9/2006 | Mataja | B62K 9/00 | 446/470 |
| 7,287,797 B1 * | 10/2007 | Belloso | B62D 21/03 | 296/193.07 |
| 7,568,962 B2 * | 8/2009 | Amadio | A63H 17/002 | 446/470 |
| 7,641,263 B2 * | 1/2010 | Ruslanov | A63H 17/002 | 446/470 |
| 8,574,022 B2 * | 11/2013 | Grisolia | A63H 17/004 | 446/437 |
| 9,393,922 B2 * | 7/2016 | Larner | B60R 11/04 | |
| 9,440,159 B1 * | 9/2016 | Vreugdenhil | A63H 29/22 | |
| 9,579,585 B2 * | 2/2017 | Silverglate | A63H 17/26 | |
| 11,786,418 B1 * | 10/2023 | Aceros | B60D 1/01 | 180/268 |
| 2005/0052080 A1 * | 3/2005 | Maslov | H02K 16/04 | 307/10.1 |
| 2006/0205317 A1 * | 9/2006 | Benassi | A63H 17/002 | 446/95 |
| 2007/0202773 A1 * | 8/2007 | Yuen | A63H 17/002 | 446/94 |
| 2008/0251249 A1 * | 10/2008 | Carlson | E21B 33/16 | 166/285 |

* cited by examiner

MODULAR MEDICAL MOBILITY DEVICE

CROSS-REFERENCE TO RELATED APPLICATIONS

This nonprovisional application is a continuation of and claims priority to U.S. patent application Ser. No. 17/247,346, now U.S. Pat. No. 11,786,418, entitled "MODULAR MEDICAL MOBILITY DEVICE," filed Dec. 8, 2020 by the same inventors, which claims priority to U.S. Provisional Patent Application No. 62/945,656, entitled "SELF-DIRECTED MODULAR MOBILITY DEVICE," filed Dec. 9, 2019 by the same inventors, all of which are incorporated herein by reference, in their entireties, for all purposes.

FEDERALLY SPONSORED RESEARCH OR DEVELOPMENT

This invention was made with Government support under Grant Nos. 1R25HD087971 and 1R25HD094335 awarded by the National Institutes of Health (NIH). The government has certain rights in the invention.

BACKGROUND OF THE INVENTION

1. Field of the Invention

This invention relates, generally, to rehabilitative medical mobility devices. More specifically, it relates to a reconfigurable system of modules that make up a battery-powered medical mobility vehicle for rehabilitation and developmental purposes.

2. Brief Description of the Prior Art

There is an underdeveloped market for products to support children and young adults with disabilities, predominantly concerning their freedom of mobility. Current devices that attempt to provide children and young adults with an increased degree of freedom include conventional ride-on toys (such as motorized or manually-operated vehicles designed to accommodate one or more children therein as operators or passengers) and powered wheelchairs; however, there are several limitations concerning each of these devices, particularly for children with disabilities.

Conventional ride-on devices are not designed for long term use and often seen as toys rather than necessities. As a result, ride-on devices are typically small, cramped, non-adjustable, and use traditional control mechanisms that may be inoperable or extremely difficult to operate or enjoy, particularly for children and young adults with disabilities or debilitating neurological diseases. Furthermore, traditional mobility devices fail to consider that children and young adults tend to continually grow, such that they typically outgrow conventional mobility devices every few months or years. Consequently, families are forced to regularly upgrade their child's mobility device to larger models when children and young adults no longer fit in their previous devices. In some instances, parents buy larger models to allow their child to grow into their new mobility device; however, in practice, such a policy results in children utilizing oversized devices that can lead to difficulty in operation. Furthermore, in situations in which the child suffers from a progressively worsening neurological condition, it is often difficult to adjust mobility devices for changing needs over time that result from the debilitating nature of the condition.

Attempts have been made to provide interchangeable parts on operable vehicles for customization post-manufacturing. For example, U.S. Pat. No. 7,100,968 B2 (the '968 patent) discloses a toy vehicle having interchangeable body styles. In particular, the '968 patent teaches a child-sized toy for which several stylistically different body modules can be removably secured. However, such devices as those disclosed in the '968 patent fail to provide the necessary adjustability, support, and autonomous guidance that children and adults with developmental and physical disabilities require as part of their prescribed therapy. In particular, the '968 patent simply provides stylistically different interchangeable vehicle body modules rather than the robust adjustability of the devices functional controls.

In addition, attempts have been made to provide modular toy car apparatuses capable of being coupled to a chassis. For example, U.S. Pat. No. 9,579,585 B2 (the '585 patent) provides a toy car system that comprises several components such as a front and rear suspension, body components, fasteners, wheels, and frame. However, such devices fail to provide the necessary adjustment for children and adults with developmental and physical disabilities. Specifically, such devices like the '585 patent do not provide leg, neck, or spinal support and adjustment. Moreover, they similarly fail to provide simple controls that children and adults can operate no matter their disability.

Accordingly, what is needed is a mobility device that is capable of adjustments and adaptations to an operator's continually changing needs while remaining simple, intuitive, and comfortable. However, in view of the art considered as a whole at the time the present invention was made, it was not obvious to those of ordinary skill in the field of this invention how the shortcomings of the prior art could be overcome.

SUMMARY OF THE INVENTION

The long-standing but heretofore unfulfilled need, stated above, is now met by a novel and non-obvious invention disclosed and claimed herein. In an aspect, the present disclosure pertains to a modular mobility device that is adjustable based on one or more body dimensions and needs of an operator is now met by a new, useful, and nonobvious invention.

The novel structure includes a medical mobility device configured for use by an operator having a developmental or physical disability. The medical mobility device comprises a chassis having a first end opposite a second end. The chassis including a plurality of links disposed between the first end and the second end. The plurality of links residing within a first plane and a plurality of mounting points extending in a direction away from the plurality of links, such that the plurality of mounting points resides within a second plane that is perpendicular to the first plane.

A plurality of reconfigurable modules is each removably received within at least one mounting point of the plurality of mounting points. The plurality of reconfigurable modules includes a front-end module, a drive module, and a power module. The front-end module includes a frame having a frame aperture formed within a bottom surface thereof. The frame aperture is configured to receive at least a portion of a caster wheel extension of a caster wheel. The frame further includes a frame extension removably received within a first mounting point of the plurality of mounting points. The first mounting point disposed at the first end of the chassis and is a first chassis aperture. An overall length of the medical mobility device is adjustable by a translation of the frame extension within the first chassis aperture.

A drive module includes a drive shaft having a first end and a second end. The first end of the drive shaft is in mechanical communication with a drive wheel and the second end of the drive shaft in mechanical communication with a motor. The drive module further including a drive module extension received within a second mounting point of the plurality of mounting points. The second mounting point is disposed in an underlying relation at the second end of the chassis. The second mounting point is a second chassis aperture, wherein the motor is adapted to impart axial rotation onto the drive wheel via the rotation of the drive shaft, such that the medical mobility device is translatable along a surface when the drive shaft is rotated.

A power module disposed between the first end and the second end of the chassis in an underlying relation to the chassis. The power module includes a support having a first end opposite a second end. The second end of the support received within a third mounting point of the plurality of mounting points. The third mounting point extending from a bottom surface of the chassis and is a third chassis aperture. A base is perpendicularly secured to the first end of the support, such that the base resides within a third plane that is parallel to the first plane of the chassis. Furthermore, a power supply is secured within the power module. The power supply resides between the base and the chassis, wherein the power supply is in electrical communication with and is configured to supply an amount of power to the motor. The medical mobility device is configured to transport the operator along the surface.

In an embodiment, the power supply is a battery configured to supply an amount of electrical energy to the power. The motor converts the electrical energy to mechanical energy to propel the medical mobility device along the surface.

In an embodiment, a second drive module is provided and is spaced apart from the first drive module. The second drive module is disposed at the second end of the chassis and is in an underlying relation to the chassis. The second drive module including a second drive shaft having a first end and a second end. The first end of the second drive shaft is in mechanical communication with a second drive wheel. The second end of the drive shaft in mechanical communication with a second drive motor. Such that the first drive module and the second drive module share a common central longitudinal axis and are configured to operate independently from one another, such that the medical mobility device has a zero-turn radius.

In yet another embodiment, the medical mobility device comprises a hitch coupled at the second end of the chassis, such that the hitch is disposed between the second end of the chassis and the drive module. An attachment is slidably received within the hitch and configured to secure a medical oxygen tank to the chassis. The medical oxygen tank is adapted to supply an amount of oxygen to the operator during operation of the medical mobility device.

In an embodiment, a leg support module is provided that includes an adduction bar having an origination end opposite a terminal end. The terminal end is configured to be secured within a fourth mounting point of the plurality of mounting points. The fourth mounting point extends upwardly from an upper surface of the chassis and is a fourth chassis aperture. The origination end of the adduction bar is adapted to be disposed between the operator's legs, such that the adduction bar prevents the operator's legs from being disposed toward a central longitudinal axis of the adduction bar.

In yet another embodiment, the plurality of modules further includes a leg support module having a first adduction bar and a second abduction bar. Each of the first and the second abduction bars have an origination end opposite a terminal end. The terminal ends are configured to be secured within a fifth and a sixth mounting points respectively. Each of the fifth and sixth mounting points extend upwardly from an upper surface of the chassis. In particular, the fifth mounting point being a fifth chassis aperture and the sixth mounting point being a sixth chassis aperture. Each of the first and the second abduction bars is adapted to be disposed between a side of the leg support module and the operator, such that each of the first and the second abduction bars is adapted to prevent the operator's legs from reaching the side of the leg support module.

A seating module is provided in another embodiment having a support bar. The support bar includes a first end opposite a second end. The first end of the support bar is coupled to a seventh mounting point of the plurality of mounting points and the seventh mounting point residing above the power module. The seventh mounting point is an outer surface of a first link of the chassis. The second end of the support bar coupled an eighth mounting point of the plurality of mounting points. The eighth mounting point resides above the power module and is an outer surface of a second link of the chassis. Moreover, the first link is different than the second link. The seating module further comprises a first platform and a second platform. Each of the first and the second platforms are coupled to a portion of the support bar and configured to rotate about the support bar. In such an embodiment, the platforms allow the operator to adjust an angle $\alpha$ formed between each of the first and the second platforms.

In an embodiment, a seat support extension having a first end opposite a second end is provided. The first end is coupled to a ninth mounting point disposed above the power module. The ninth mounting point is an outer surface of a third link of the chassis, wherein the third link is different from each of the first and the second links. The first platform includes a first angled platform and a second angled platform. Each of the first and second angled platforms are coupled to the seat support extension respectfully, thereby permitting the operator to adjust an angle $\beta$ formed between each of the first and second angled platforms.

An embodiment of the medical mobility device includes a harness module including a harness support bar having a first end opposite a second end. The first end of the harness support bar has a first channel mount slidably disposed over a tenth mounting point. The tenth mounting point is disposed between the power module and the second end of the chassis and is an outer surface of a first link of the chassis. The second end of the harness support bar includes a second channel mount slidably disposed over an eleventh mounting point of the plurality of mounting points. The eleventh mounting point is an outer surface of a second link of the chassis. Furthermore, a harness is coupled to a portion of the harness support bar, wherein the harness is configured to secure the operator within the medical mobility device. In such embodiment, the harness is selected from the group consisting of a 4-point harness, a helmet, a lap bar, and a 2-point harness.

In an embodiment, the power module includes a plurality of removable sides coupled to the support of the power module. Each of the plurality of removable sides spans from the first end to the second end thereof. The plurality of removable sides prevents foreign objects from damaging the power supply housed within the power module during operation of the medical mobility device.

In yet another embodiment, a medical mobility device is provided comprising a chassis having a first end opposite a second end. The chassis includes a plurality of links disposed between the first end and the second end. A plurality of mounting points are in mechanical communication with the plurality of links, such that each link of the plurality of links is coupled to at least one mounting point of the plurality of mounting points. Each mounting point of the plurality of mounting points is selected from a group consisting of an outer surface of the link, a receiving aperture, and an internal channel of the link.

A front end module is secured to the chassis and includes a frame having a frame aperture formed within a bottom surface thereof. The frame aperture is configured to receive at least a portion of a caster wheel, wherein the caster wheel is in operable communication with a surface. A frame extension in mechanical communication with the chassis. The frame extension has an outer diameter that is smaller than an internal diameter of a first mounting point of the plurality of mounting points of the chassis. The first mounting point is an internal channel of one of the plurality of links of the chassis, such that the frame extension of the front end module is at least partially slidably received within the first mounting point. An overall length of the medical mobility device is adjustable by a translation of the frame extension within the first mounting point.

A drive module is secured to the chassis having a drive wheel inoperable communication with the surface. A drive shaft includes a first end and a second end, the first end of the drive shaft in mechanical communication with the drive wheel and the second end of the drive shaft in mechanical communication with a motor. The motor is adapted to impart axial rotation onto the drive wheel via rotation of the drive shaft. Additionally, a drive module extension is in mechanical communication with the chassis. The drive module extension extends away from the motor toward a second mounting point of the chassis. The second mounting point is a receiving aperture disposed in an underlying relation at the second end of the chassis and is configured to receive at least a portion of the drive module extension. By coupling the drive module to the chassis, the medical mobility device is translatable along the surface when the drive shaft is rotated.

A harness module is provided having a harness support bar in mechanical communication with the chassis. The harness support bar extends upwardly from the chassis from a proximal end to a distal end. A harness is coupled to a portion of the harness support bar between the proximal end and the distal end of the harness support bar. Furthermore, a channel mount is in mechanical communication with a third mounting point of the chassis being an outer surface of a link. The channel mount is configured to be slidably disposed over the outer surface of the link, thereby coupling the harness module to the chassis, such that the harness module is translatable along the outer surface of the link.

In yet another embodiment, a medical mobility device for use by a patient having a developmental or physical disability is provided. The medical mobility device comprises a chassis having a first end opposite a second end. The chassis including a plurality of links disposed between the first end and the second end. The plurality of links resides within a first plane and a plurality of mounting points extends in a direction away from the plurality of links, such that the plurality of mounting points resides within a second plane that is perpendicular to the first plane.

A plurality of reconfigurable modules each removably received within at least one mounting point of the plurality of mounting points are provided. Specifically, a front-end module is secured to the chassis. The front-end module including a frame having a frame aperture formed within a bottom surface thereof. The frame aperture is configured to receive at least a portion of a caster wheel extension of a caster wheel. The frame further includes a frame extension that is removably received within a first mounting point of the plurality of mounting points. The first mounting point is disposed at the first end of the chassis and is a first chassis aperture. An overall length of the medical mobility device is adjustable by a translation of the frame extension within the first chassis aperture.

A drive module includes a drive shaft having a first end and a second end. The first end of the drive shaft is in mechanical communication with a drive wheel and the second end of the drive shaft in mechanical communication with a motor. The drive module further includes a drive module extension received within a second mounting point of the plurality of mounting points. The second mounting point is disposed in an underlying relation at the second end of the chassis and is a second chassis aperture. The motor is adapted to impart axial rotation onto the drive wheel via the rotation of the drive shaft, such that the medical mobility device is translatable along a surface when the drive shaft is rotated.

A power module is disposed between the first end and the second end in an underlying relation to the chassis. The power module includes a support having a first end opposite a second end, the second end received within a third mounting point of the plurality of mounting points. The third mounting point extending from a bottom surface of the chassis, the third mounting point being a third chassis aperture.

A base is perpendicularly secured to the first end of the support and resides within a third plane that is parallel to the first plane of the chassis.

A power supply secured within the power module. The power supply resides between the base and the chassis, wherein the power supply is in electrical communication with and is configured to supply an amount of power to the motor.

A body module has a front end and a rear end. Each of the front end and the rear end is configured to be disposed over at least a portion of the chassis.

A control module is in mechanical communication within the front end of the body module and includes a control bar configured to receive an operator control accessory thereon. The operator control accessory adapted to receive an input from the operator, wherein the operator controls the medical mobility device via the operator control accessory.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not restrictive.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the invention, reference should be made to the following detailed description, taken in connection with the accompanying drawings, in which.

DETAILED DESCRIPTION OF THE INVENTION

Figure 1A:
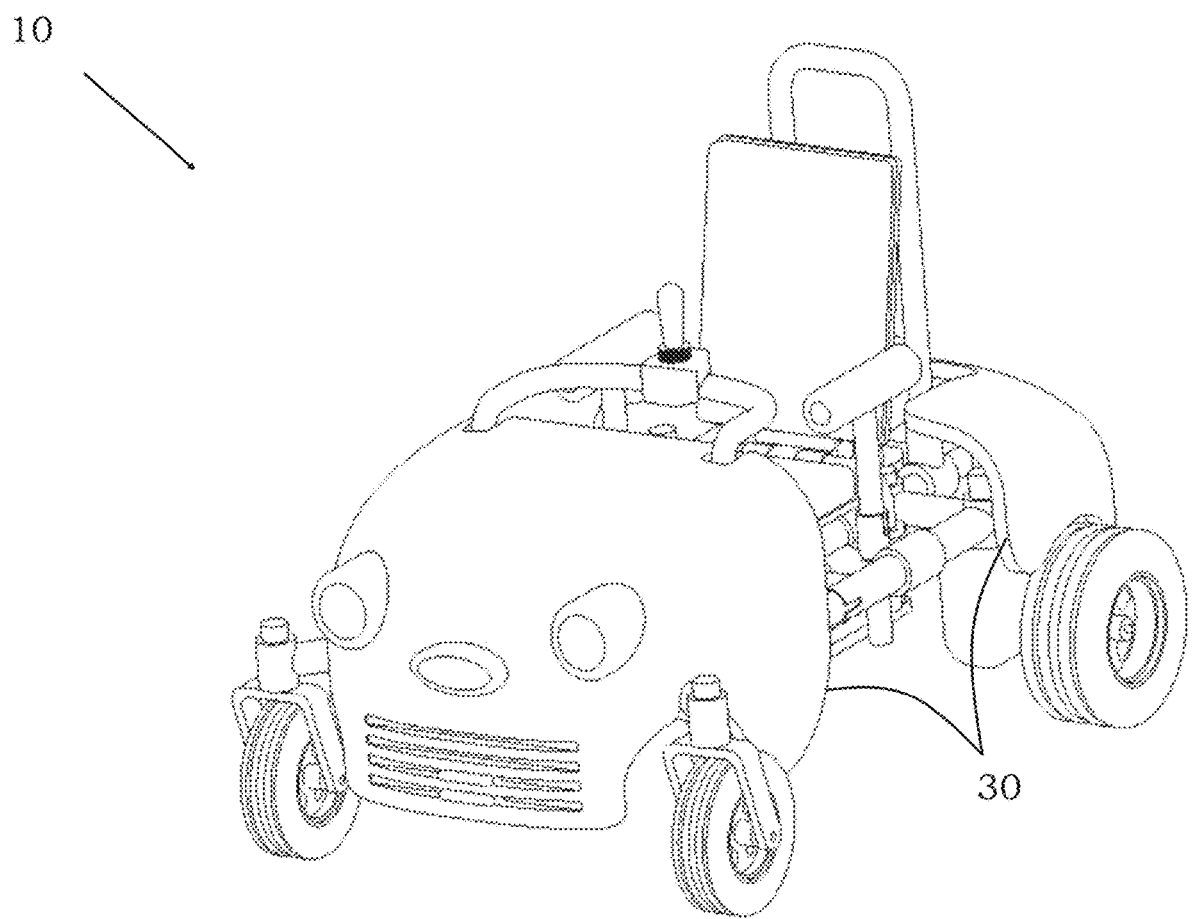
FIG. 1A is a front perspective view of the medical mobility device, according to an embodiment of the present disclosure.

In the following detailed description of the preferred embodiments, reference is made to the accompanying drawings, which form a part thereof, and within which are shown by way of illustration specific embodiments by which the invention may be practiced. It is to be understood that one skilled in the art will recognize that other embodiments may be utilized, and it will be apparent to one skilled in the art that structural changes may be made without departing from the scope of the invention. Elements/components shown in diagrams are illustrative of exemplary embodiments of the disclosure and are meant to avoid obscuring the disclosure. Any headings used herein are for organizational purposes only and shall not be used to limit the scope of the description or the claims. Furthermore, the use of certain terms in various places in the specification, described herein, are for illustration and should not be construed as limiting.

Reference in the specification to "one embodiment," "preferred embodiment," "an embodiment," or "embodiments" means that a particular feature, structure, characteristic, or function described in connection with the embodiment is included in at least one embodiment of the disclosure and may be in more than one embodiment. The appearances of the phrases "in one embodiment," "in an embodiment," "in embodiments," "in alternative embodiments," "in an alternative embodiment," or "in some embodiments" in various places in the specification are not necessarily all referring to the same embodiment or embodiments. The terms "include," "including," "comprise," and "comprising" shall be understood to be open terms and any lists that follow are examples and not meant to be limited to the listed items.

Definitions

As used in this specification and the appended claims, the singular forms "a," "an," and "the" include plural referents unless the content clearly dictates otherwise. As used in this specification and the appended claims, the term "or" is generally employed in its sense including "and/or" unless the context clearly dictates otherwise.

As used herein, the terms "about," "approximately," or "roughly" as used herein refer to being within an acceptable error range for the particular value as determined by one of ordinary skill in the art, which will depend in part on how the value is measured or determined (i.e., the limitations of a measurement system), (i.e., the degree of precision required for a particular purpose, such as producing a modular medical mobility device). As used herein, "about," "approximately," or "roughly" refer to within +15% of the numerical.

All numerical designations, including ranges, are approximations which are varied up or down by increments of 1.0, 0.1, 0.01 or 0.001 as appropriate. It is to be understood, even if it is not always explicitly stated, that all numerical designations are preceded by the term "about". It is also to be understood, even if it is not always explicitly stated, that the compounds and structures described herein are merely exemplary and that equivalents of such are known in the art and can be substituted for the compounds and structures explicitly stated herein.

Wherever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Wherever the term "no more than," "less than," or "less than or equal to" precedes the first numerical value in a series of two or more numerical values, the term "no more than," "less than" or "less than or equal to" applies to each of the numerical values in that series of numerical values. For example, less than or equal to 1, 2, or 3 is equivalent to less than or equal to 1, less than or equal to 2, or less than or equal to 3.

Modular Medical Mobility Device

The present disclosure pertains to a medical mobility device that is fully adjustable based on the operator's needs. Whether the operator is an adult suffering from a neurological disease or a child with a developmental disability, the medical mobility device is continuously adaptable to their ever-changing needs and medical conditions. In particular, the medical mobility device includes a series of modules that couple to a single, central chassis for support. Each of the modules caters to a specific functionality that may require adjustment or modified support for the operator.

Specifically, the medical mobility device includes a chassis with a plurality of mounting points that are designed to secure to various modules. Modules such as seating modules, control modules, harness modules, footrest modules, and leg support modules are critical for providing ease of use and comfort for the operator; moreover, such modules benefit from the ability to be continuously adjusted based on the operator's needs. For example, the harness module is configured to secure the operator within the seating module to prevent the operator from being ejected from the medical mobility device. Securing the operator within the seating module is critical, particularly for operators who suffer from a lack of control or mobility of their body. More specifically, if an operator loses significant motor function in the head and neck region, they can lose the ability to control their head's placement. To account for this, the harness module may contain a helmet or headrest that supports the head of the operator and naturally aligns their vision to control the operation of the medical mobility device. In yet another example, leg support modules can include adjustable adduction or abduction bars to ensure that the operator's legs are correctly aligned and do not drift too far or too close to the midline of the operator's body, further securing the operator within the medical mobility device.

Moreover, each of these modules are entirely adjustable, thereby providing a wide range of adjustability. Thus, in a child's case, the modules can be continuously adjusted as the child grows, rather than requiring routine replacement of an existing device each time the child has a growth spurt. Additionally, in the case of a degenerative neurological disease that progressively worsens over time, the modules of the medical mobility device can be adjusted as the operator loses body function and control. These modules and the coupling mechanisms between the modules and the chassis will be described in the sections below.

Figure 1B:
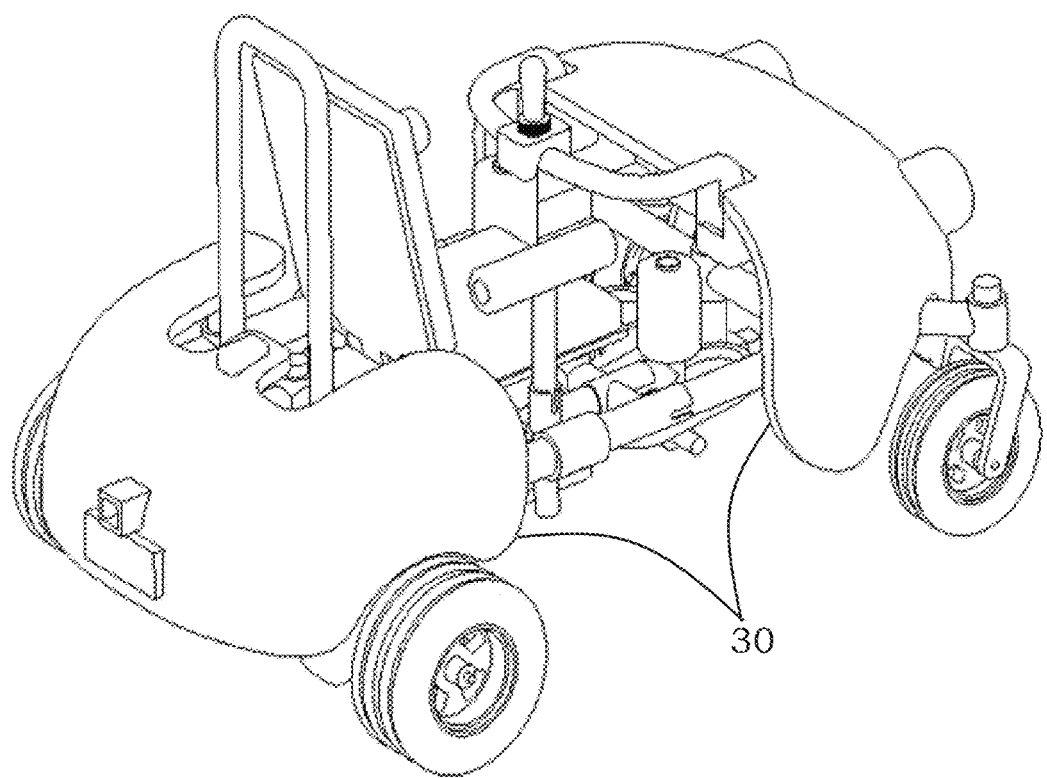
FIG. 1B is a rear perspective view of the medical mobility device, according to an embodiment of the present disclosure.
Figure 2:
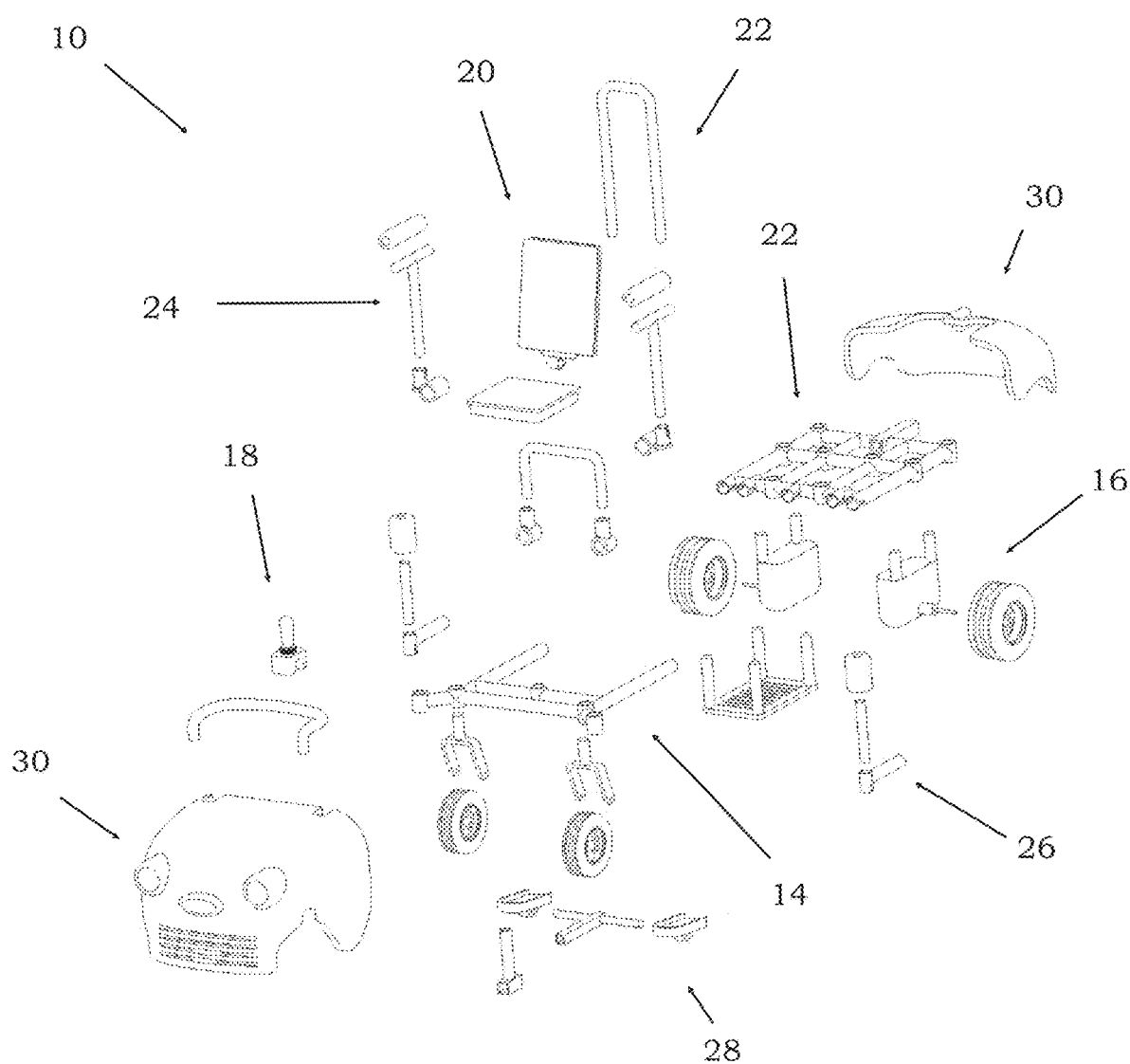
FIG. 2 is an exploded view of the medical mobility device depicting several adjustable modules, according to an embodiment of the present disclosure.

Referring generally to FIGS. 1A-2, modular therapeutic and rehabilitation device (hereinafter "medical mobility device") 10 comprises chassis 12 removably coupled to one or more of the following modules: front end module 14, drive module 16, control module 18, seating module 20, harness module 22, armrest module 24, leg support module 26, footrest module 28, and body modules 30 (collectively referred to as "modules" and will each be discussed in greater detail below). Medical mobility device 10 is adjustable depending on the operator's (i.e., children and adults with developmental challenges or child and adults with mobility issues) body measurements, such as weight, height, and overall build.

Furthermore, medical mobility device 10 is customizable based on the operator's preferred position of the modules and corresponding controls. By providing for a wide range of adjustments, medical mobility device 10 is adjustable based on the continuing needs of the operator. Moreover, these adjustments allow the operator to grow with and develop a high level of comfort and familiarity with the operation and control of medical mobility device 10. With conventional devices, once an operator outgrows the equipment, they are forced to upgrade to a different device to accommodate the operator's growing body measurements or disease progression. This constant upgrading and swapping of devices can be burdensome financially on the family and emotionally on the child or adult.

For example, for children and adults with disabilities that progressively worsen over time-such as amyotrophic lateral sclerosis (ALS)—having a medical mobility device 10 that is adapted to adjust based on the operator's disease is critical. ALS, also known as motor neuron disease or Lou Gehrig's disease, weakens a person's muscles and impacts their physical function. Having an adjustable medical mobility device 10 capable of adapting to the operator's changing ALS symptoms lessens the overall cost burden on families and provide a greater level of comfort, familiarity, and normalcy to the patient (e.g., operator). Specifically, as the operator's movement as a result of their ALS worsening, medical mobility device 10 adapts and is adjusted based on the disease's progression.

Chassis

Figure 3:
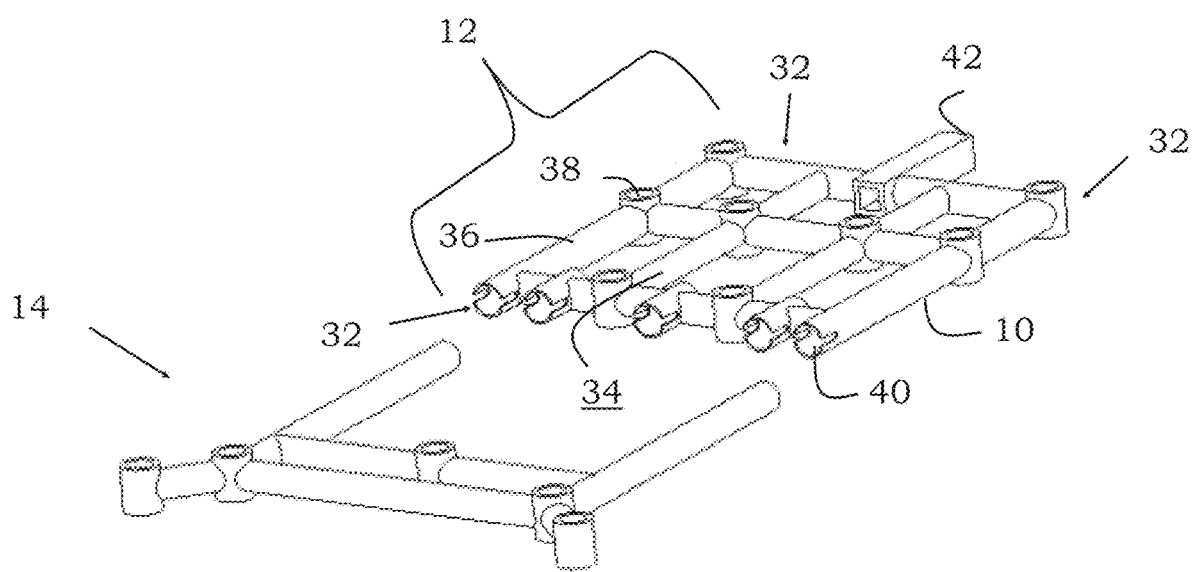
FIG. 3 is an exploded perspective view of the chassis spaced apart from a portion of the front-end module, according to an embodiment of the present disclosure.

As shown in FIG. 3, medical mobility device 10 is structurally supported by chassis 12. Chassis 12 can be formed of various materials such as wood, aluminum, steel, titanium, carbon fiber, polyvinylchloride (PVC), acrylonitrile-butadiene-styrene (ABS), or through an injection molding process. In an embodiment, chassis 12 is a reconfigurable grid comprising a series of links 36, with each link 36 being coupled (or integrally formed) with at least one mounting point 32. Mounting points 32 permit the coupling of the various modules to chassis 12. In particular, mounting points 32 may include outer surface 34 of links 36, receiving apertures 38, or internal channel 40 of links 36 and vary depending on the specific module being attached. To that end, links 36 and mounting points 32 of chassis 12 are arranged based on the desired positioning of the modules as determined by the needs of the operator. In various embodiments, modules are coupled to chassis 12 using bolts, nuts, clamps, gravity, adhesive, welding, magnetic attraction, press-fitting, pins, or other methods known in the art.

Specifically, when modules are received within receiving aperture 38, a bolt/quick-release lever is in mechanical communication with receiving aperture 38 to secure modules to chassis 12. Furthermore, each of the modules is electrically coupled to one another and chassis 12 using wire connectors, such as a wired pigtail connector, to facilitate plug-and-play support when swapping modules and features. Additionally, electrical connectors may be integrated into the specific modules mechanical and electrical systems to plug one module or device into another.

Figure 4:
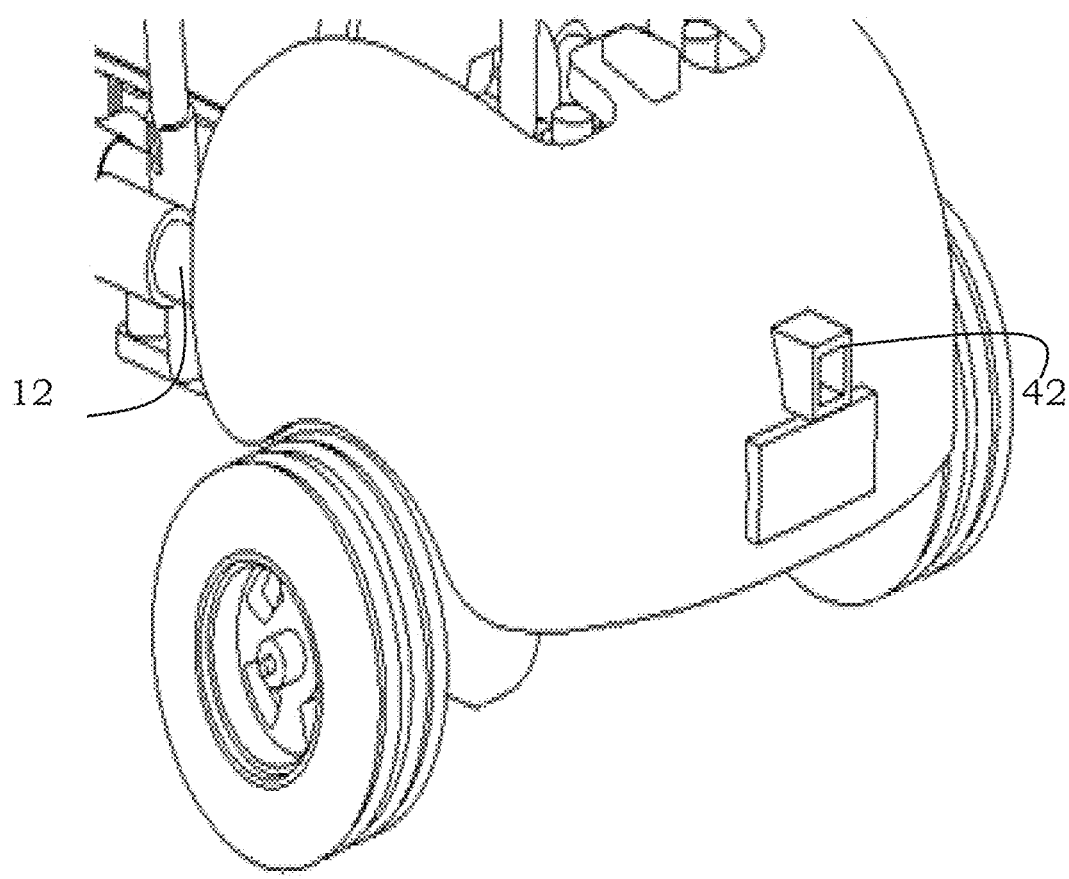
FIG. 4 is a perspective view of the medical mobility device depicting the hitch receiver coupled to the chassis and disposed through a portion of the rear body cover, according to an embodiment of the present disclosure.

In an embodiment of chassis 12 as depicted in FIG. 4, hitch receiver 42 is monolithically formed with links 36. Hitch receiver 42 is configured to secure one or more accessories to medical mobility device 10. Accessories may include external trays, storage modules, respirator tanks, caretaker supplies, medical supplies, toys, repair tools, personal supplies, or similar detachably securable devices commonly used in combination with medical mobility device 10. For example, in situations in which operators need a constant supply of oxygen, oxygen tanks can be secured to an attachment.

Front-End Module

Figure 5:
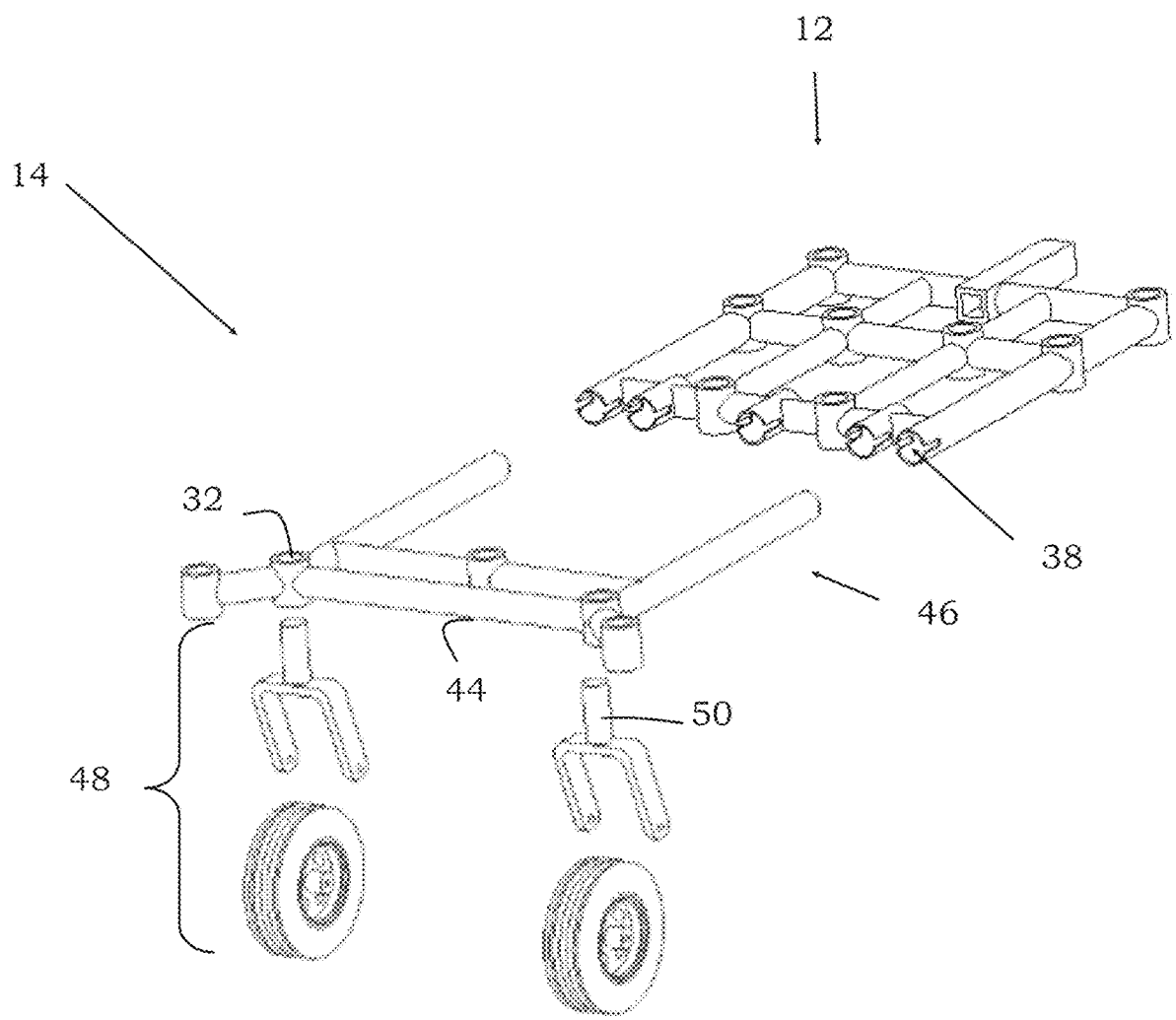
FIG. 5 depicts an exploded view of the front-end module spaced apart from the chassis, according to an embodiment of the present disclosure.

Referring to FIG. 5, a perspective view of front-end module 14 is shown and includes frame 44, having one or more mounting points 32. In an embodiment, the one or more mounting points 32 of front-end module 14 are configured to operably receive one or more wheels 48 (alternatively referred to as caster wheels 48), which can be rotatable wheels, caster wheels, or other wheels capable of horizontal translation on a ground surface. Frame 44 includes frame extensions 46 configured to be slidably disposed within receiving apertures 38 of links 36 and provide for lengthwise adjustment of medical mobility device 10. By adjusting frame extensions 46 in a direction away from wheels 48 within receiving apertures 38, the overall length of medical mobility device 10 is reduced. Consequently, adjustment of frame extensions 46 in a direction away from chassis 12 results in an increase in the overall length of medical mobility device 10. Frame extensions 46 may be secured to chassis 12 using a pin, bolt, cable, press-fit, friction, latch, nail, welding, nut, adhesive, clamp, or other securing mechanisms to prevent frame extensions 46 from being removed from within receiving apertures 38 without receiving a force.

For example, as a child with disabilities grows older and becomes progressively taller, front-end module 14 may be slidably translated within receiving apertures 38 in a direction away from chassis 12 to increase the overall length of medical mobility device 10 and accommodate for the disabled child's taller stature without having to replace medical mobility device 10 with another medical mobility device 10 of larger size.

As noted above, front-end module 14 includes a pair of wheels 48, which can be caster wheels—such as swivel casters, industrial casters, braking and locking casters, and kingpinless casters—coupled to frame 44 via mounting points 32. Caster wheels 48 enable medical mobility device 10 to translate linearly along a surface and are mounted on a pivot. Caster wheels 48 automatically align to the direction of travel when propelled by drive module 16, which will be discussed in greater detail below. Caster wheels 48 may be air-filled or solid rubber, aluminum, steel, nylon, plastic, or combinations thereof. In an embodiment as depicted in FIG. 5, caster wheels 48 include caster wheel extension 50 disposed through mounting point 32, thereby securing caster wheels 48 to chassis 12. Caster wheel extensions 50 are slidably disposed within mounting points 32 of front-end module 14 and provide vertical (i.e., height of medical mobility device 10 from the surface) adjustment.

Drive Module

Figure 6:
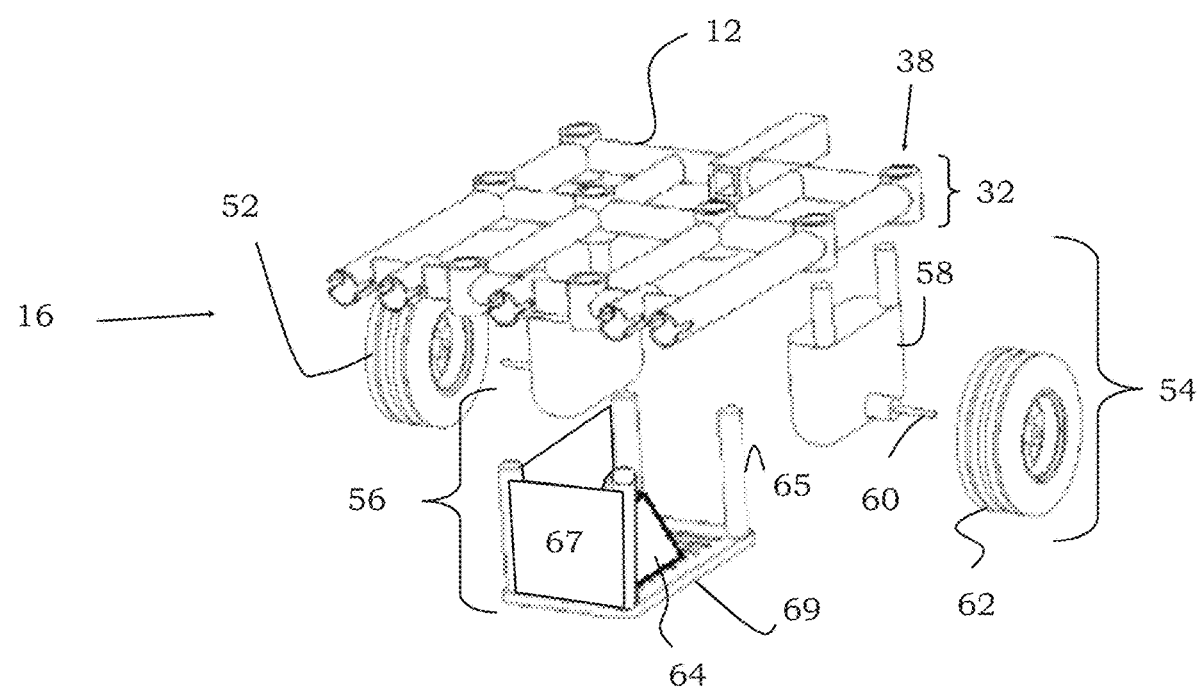
FIG. 6 depicts an exploded view of the drive module in relation to the chassis, according to an embodiment of the present disclosure.

Referring to FIG. 6, drive module 16 includes first drive wheel module 52, second drive wheel module 54, and power module 56, each of which is adjustably coupled to mounting points 32 on chassis 12. In particular, drive wheel modules 52, 54 include motor 58 in axial communication with drive shaft 60 connected to drive wheel 62. When used in conjunction with caster wheels 48, drive wheel modules 52, 54 propel medical mobility device 10 to the desired destination linearly along a surface. Each drive wheel module 52, 54 is configured to operate independently from one another. As such, by controlling the rotational speed and direction of each drive wheel 62 independently (e.g., differential steering), medical mobility device 10 is steerable having a zero-turn (z-turn) turning radius, thereby allowing an operator to have increased mobility and control of medical mobility device 10.

Power Module

Still referring to FIG. 6, power is supplied to motors 58 by battery 64 housed within power module 56. Ideally, power module 56 is disposed in underlying relation to chassis 12 and in line with an operator-such that the center of gravity of medical mobility device 10 is centered and lowered below the operator, as shown in FIG. 2. In particular, power module 56 includes base 69 having one or more supports 65 extending perpendicularly in a direction away from base 69. Supports 65 are removably received within receiving apertures 38 of mounting points 32 of chassis 12, thereby securing power module 56 to chassis 12. In an embodiment, power module 56 includes removable sides 67 coupled with supports 65 and/or base 69 to protect components residing within power module 56. Components disposed within power module 56 may include battery 64, as well as electronics and other equipment to control the various functions, sensors, and features of medical mobility device 10. In yet another embodiment, power module 56 includes an internal combustion engine, a generator, one or more photovoltaic solar cells, or other means for supplying an amount of power to battery 64 and/or directly to motors 58 themselves.

Control Module

Figure 7A:
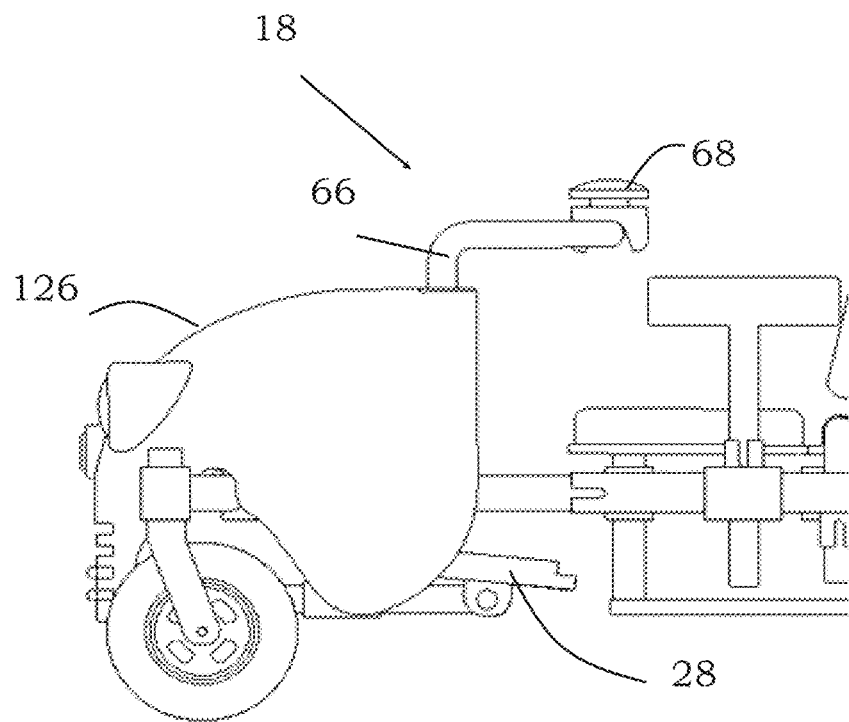
FIG. 7A depicts a side view of a portion of the medical mobility device shown in FIG. 7B and FIG. 7C, according to an embodiment of the present disclosure.
Figure 7B:
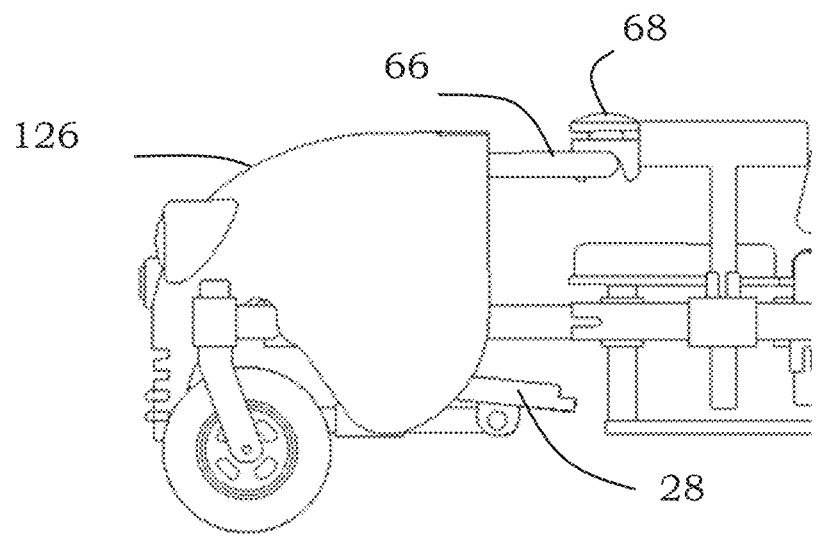
FIG. 7B depicts a side view of a portion of the medical mobility device shown in FIG. 7A and FIG. 7C, according to an embodiment of the present disclosure.
Figure 7C:
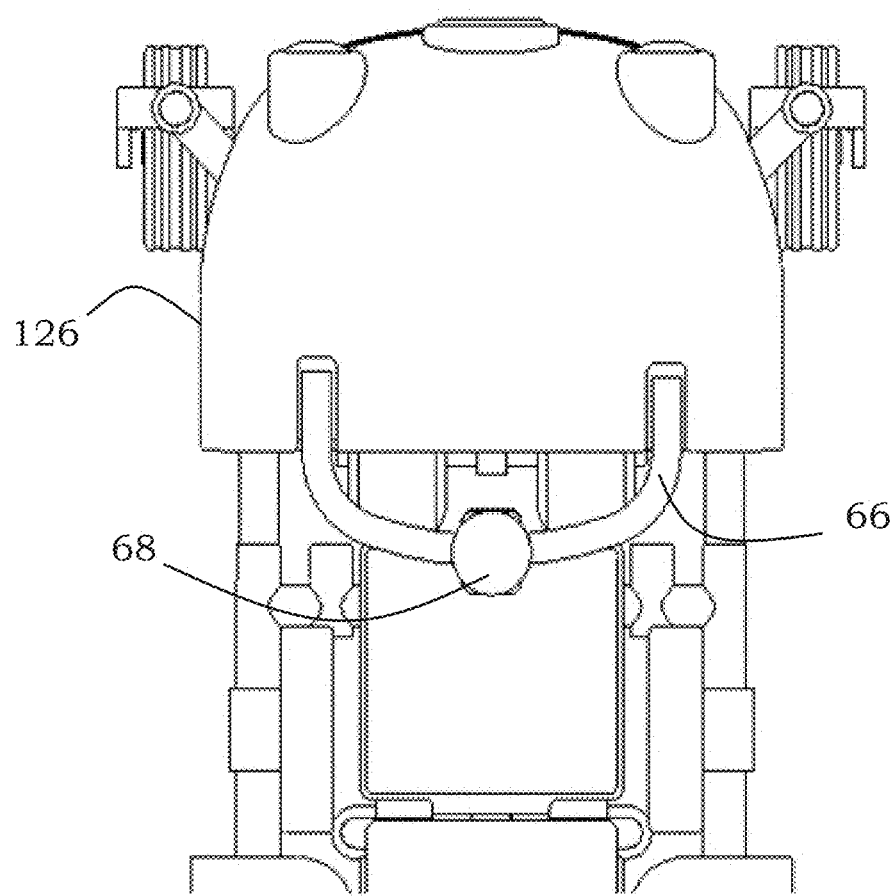
FIG. 7C depicts a top view of a portion of the medical mobility device shown in FIG. 7A and FIG. 7B, according to an embodiment of the present disclosure.
Figure 7D:
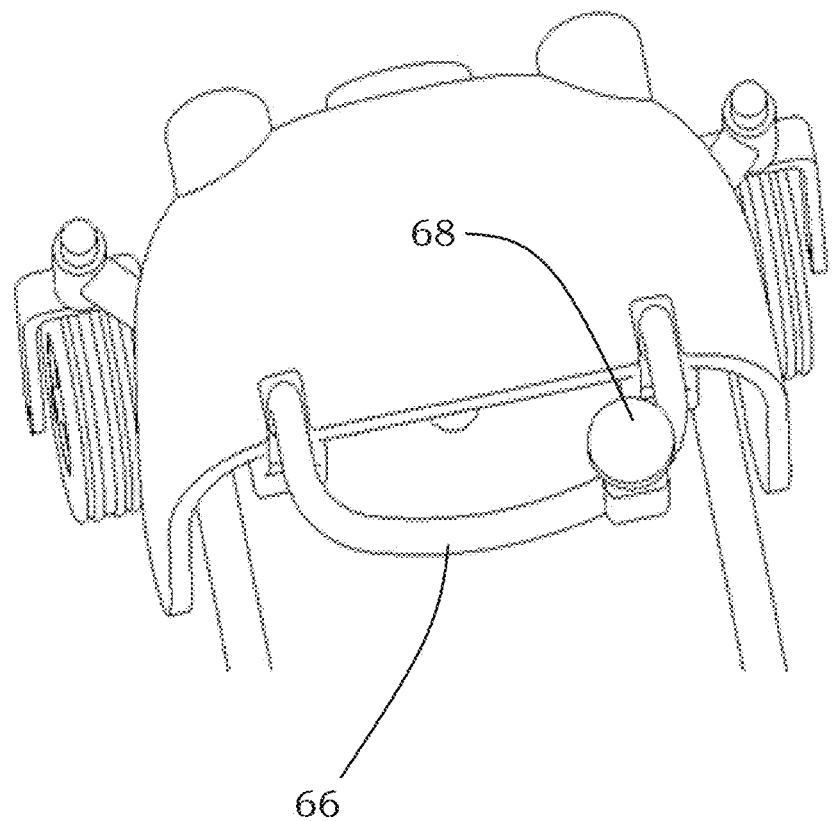
FIG. 7D depicts a top perspective view of a portion of the medical mobility device, showing the operator control accessory in a first configuration, according to an embodiment of the present disclosure.
Figure 7E:
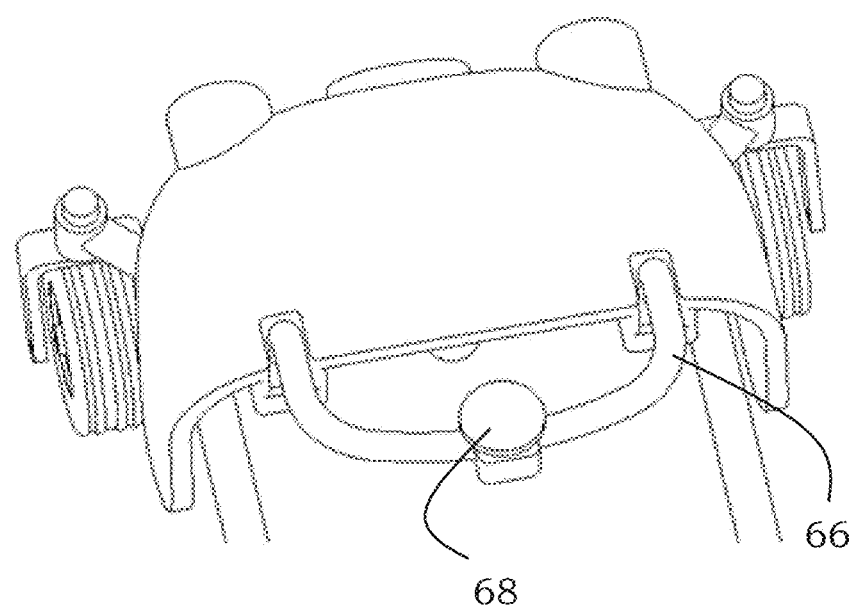
FIG. 7E depicts a top perspective view of a portion of the medical mobility device, showing the operator control accessory in a second configuration, according to an embodiment of the present disclosure.
Figure 7F:
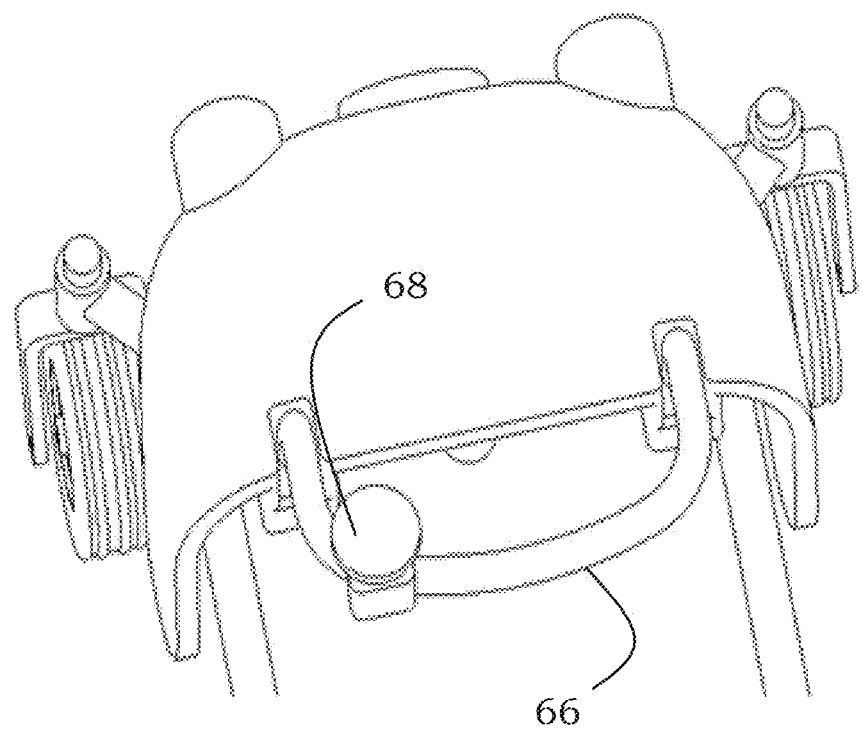
FIG. 7F depicts a top perspective view of a portion of the medical mobility device, showing the operator control accessory in a third configuration, according to an embodiment of the present disclosure.

Referring to FIGS. 7A-7F, control module 18 includes control bar 66 and operator control accessories 68 mounted onto control bar 66. Control bar 66 is secured to front body component 126 of medical mobility device 10; in alternative embodiments, control bar 66 is secured to mounting points 32 of front-end module 14 or chassis 12. Moreover, operator control accessories 68 can be disposed along the entirety of control bar 66, depending on the operator's preference. For example, FIG. 7D depicts operator control accessories 68 disposed in proximal relation to the starboard side of medical mobility device 10; FIG. 7E depicts operator control accessories 68 disposed in a central location of medical mobility device 10; and FIG. 7F depicts operator control accessories 68 disposed proximal in relation to the port side of medical mobility device 10.

In addition to the adjustable placement of operator control accessories 68, control bar 66 is configured to be adjustable along the x-axis, y-axis, and z-axis with respect to chassis 12 to permit the ideal placement of operator control accessories 68 depending on operator preference and/or physical or developmental limitations. Furthermore, as the operator's disability progresses or the operator grows, control bar 66 is capable of being adjusted over time. For example, control bar 66 is linearly translatable with respect to chassis 12, such that a distance between operator control accessories 68 and chassis 12 is adjustable depending on a height of the operator.

Figure 8A:
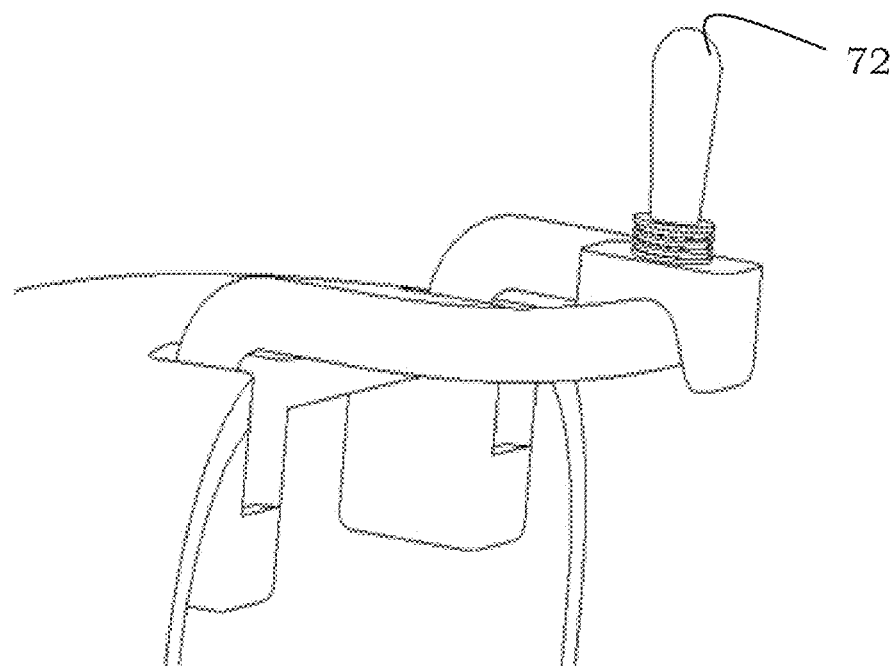
FIG. 8A is a perspective view of an embodiment of an operator control accessory in the form of a joystick, according to an embodiment of the present disclosure.
Figure 8B:
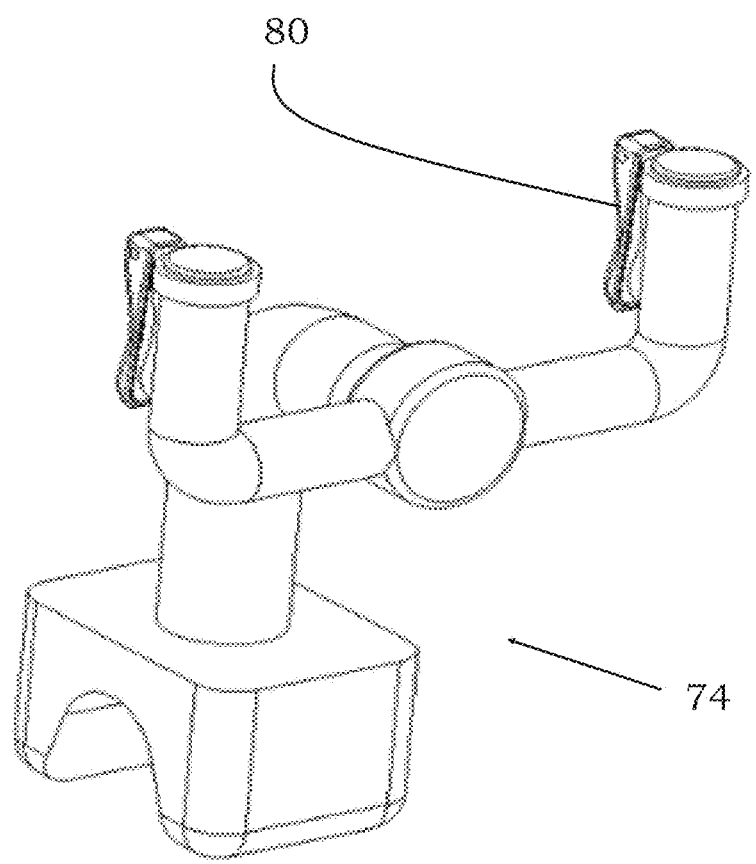
FIG. 8B is a perspective view of an embodiment of an operator control accessory in the form of a yoke, according to an embodiment of the present disclosure.
Figure 8C:
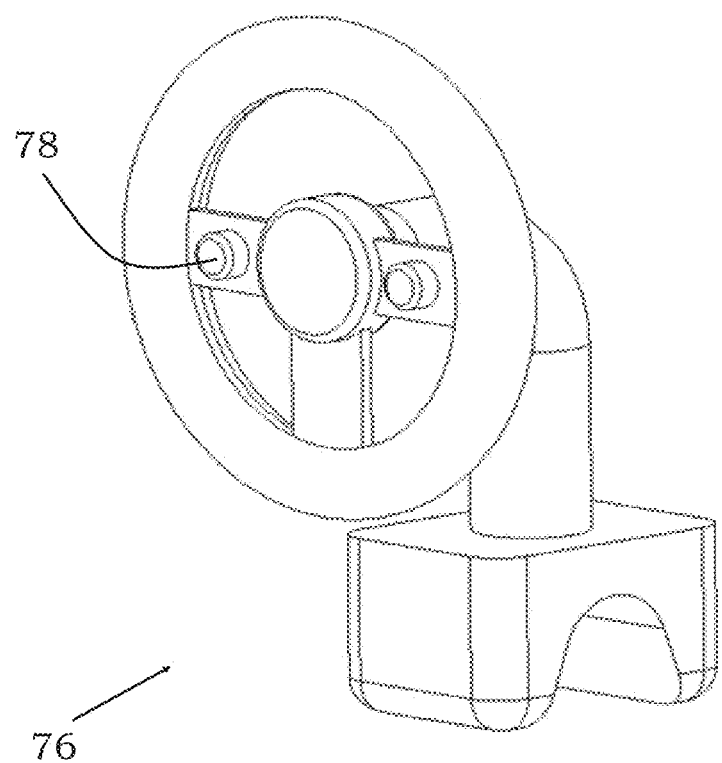
FIG. 8C is a perspective view of an embodiment of an operator control accessory in the form of a steering wheel, according to an embodiment of the present disclosure.
Figure 8D:
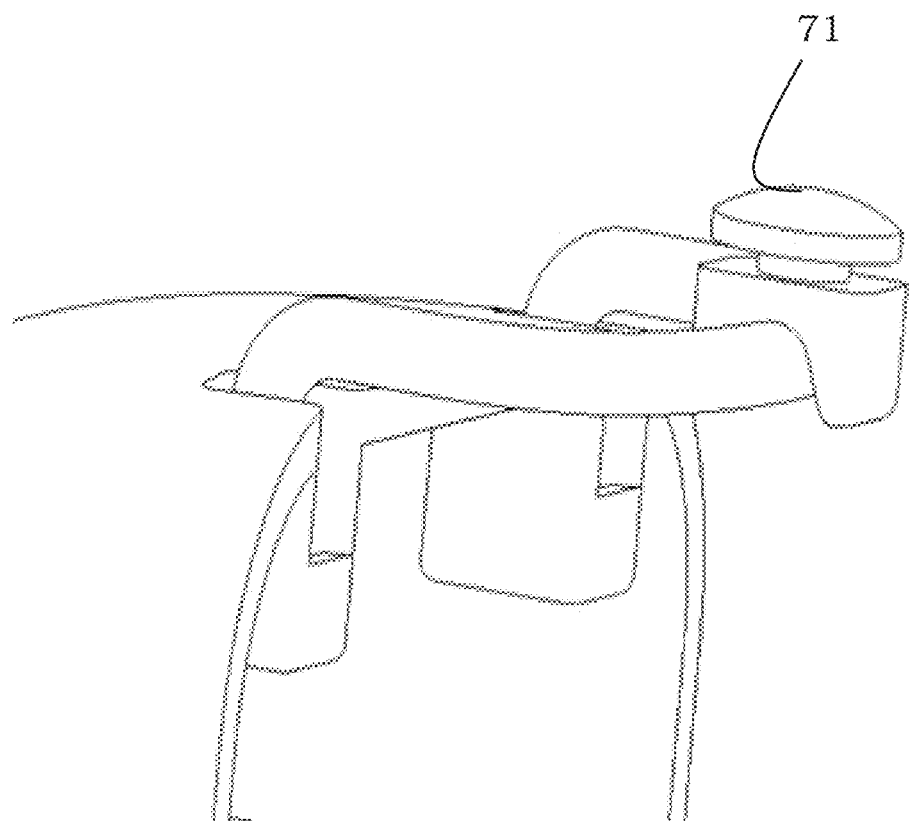
FIG. 8D is a perspective view of an embodiment of an operator control accessory in the form of a push-button, according to an embodiment of the present disclosure.

Operator control accessories 68 are configured to control various operations of medical mobility device 10, including lighting, steering, speed, music, and other similar features. As depicted in FIGS. 8A-8C, operator control accessories 68 may be in the form of a joystick 72, yoke 74, steering wheel 76, or push button 71; in addition, depending on the requirements of the operator, the particular accessory implemented on medical mobility device 10 can be interchanged, such that joystick 72 and be replaced by yoke 74 if desired. In some embodiments, buttons 78 or levers 80 control steering, acceleration, and/or braking of medical mobility device 10 and may be used with operator control accessories 68. In yet further embodiments, acceleration and braking may be controlled using footrest modules 28, which will be described in greater detail below.

Seating Module

Figure 9A:
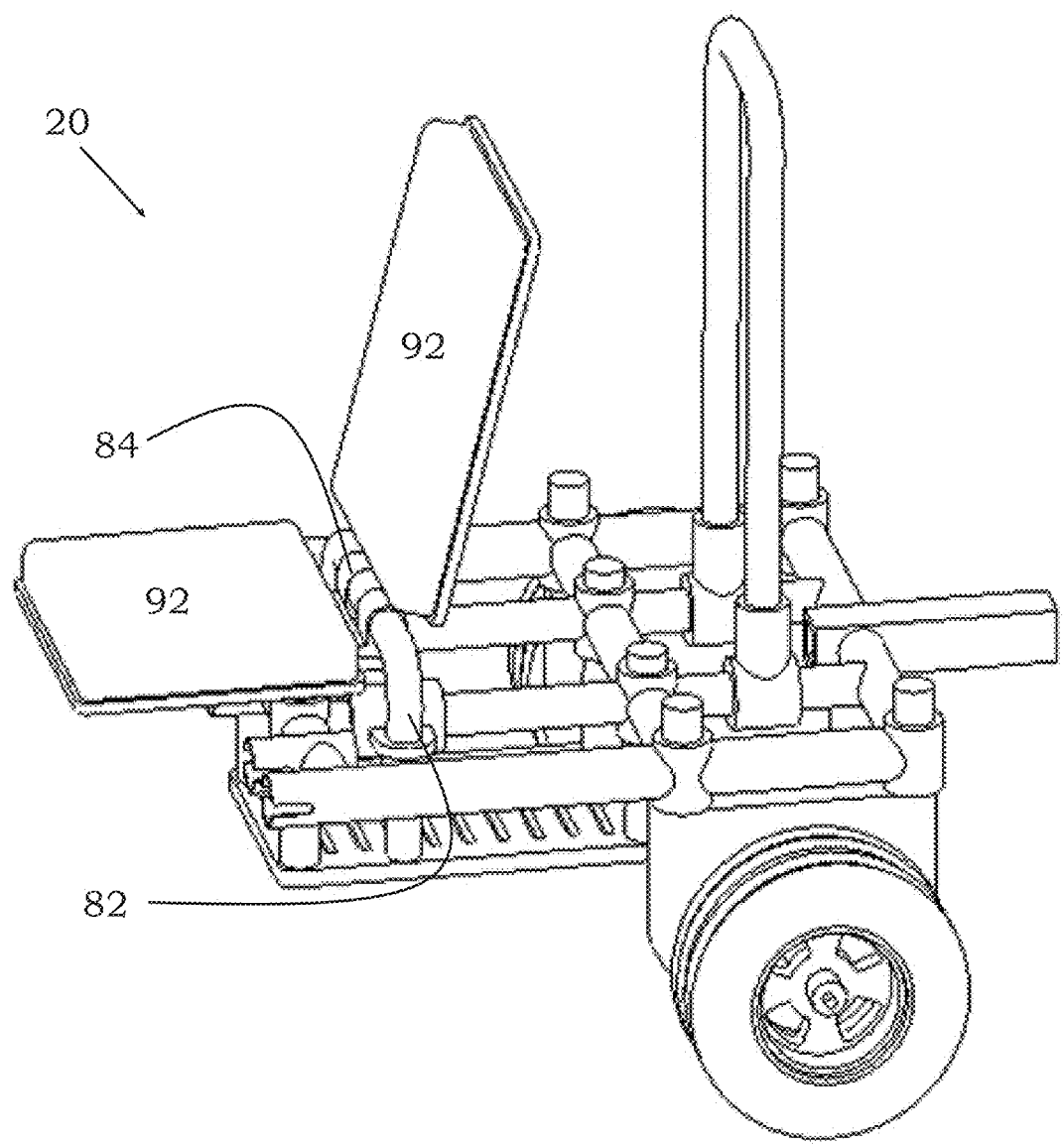
FIG. 9A is a perspective view of a portion of the medical mobility device showing the seat module in a first horizontal position, according to an embodiment of the present disclosure.
Figure 9B:
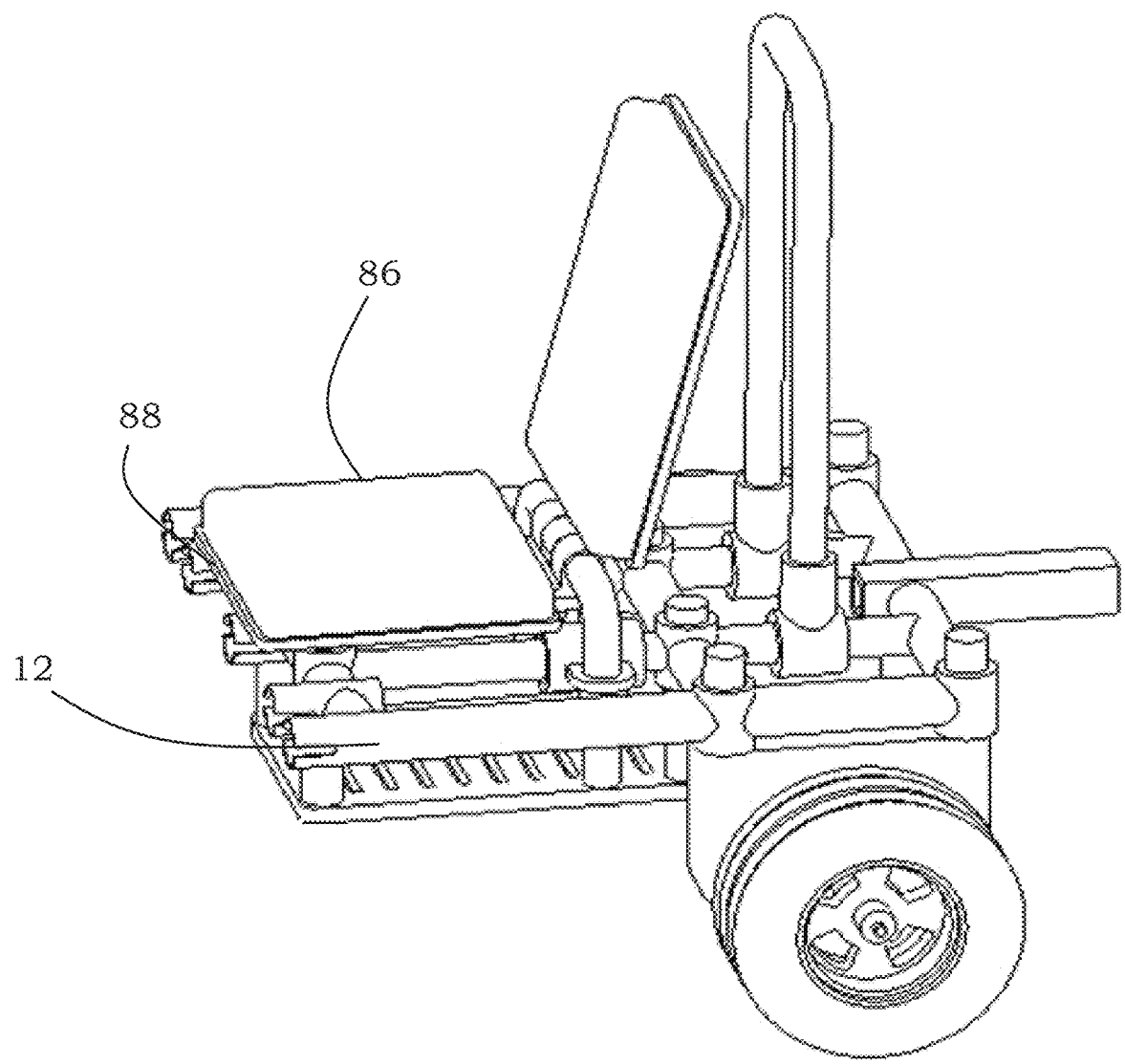
FIG. 9B is a perspective view of a portion of the medical mobility device showing the seat module in a second horizontal position, according to an embodiment of the present disclosure.
Figure 9C:
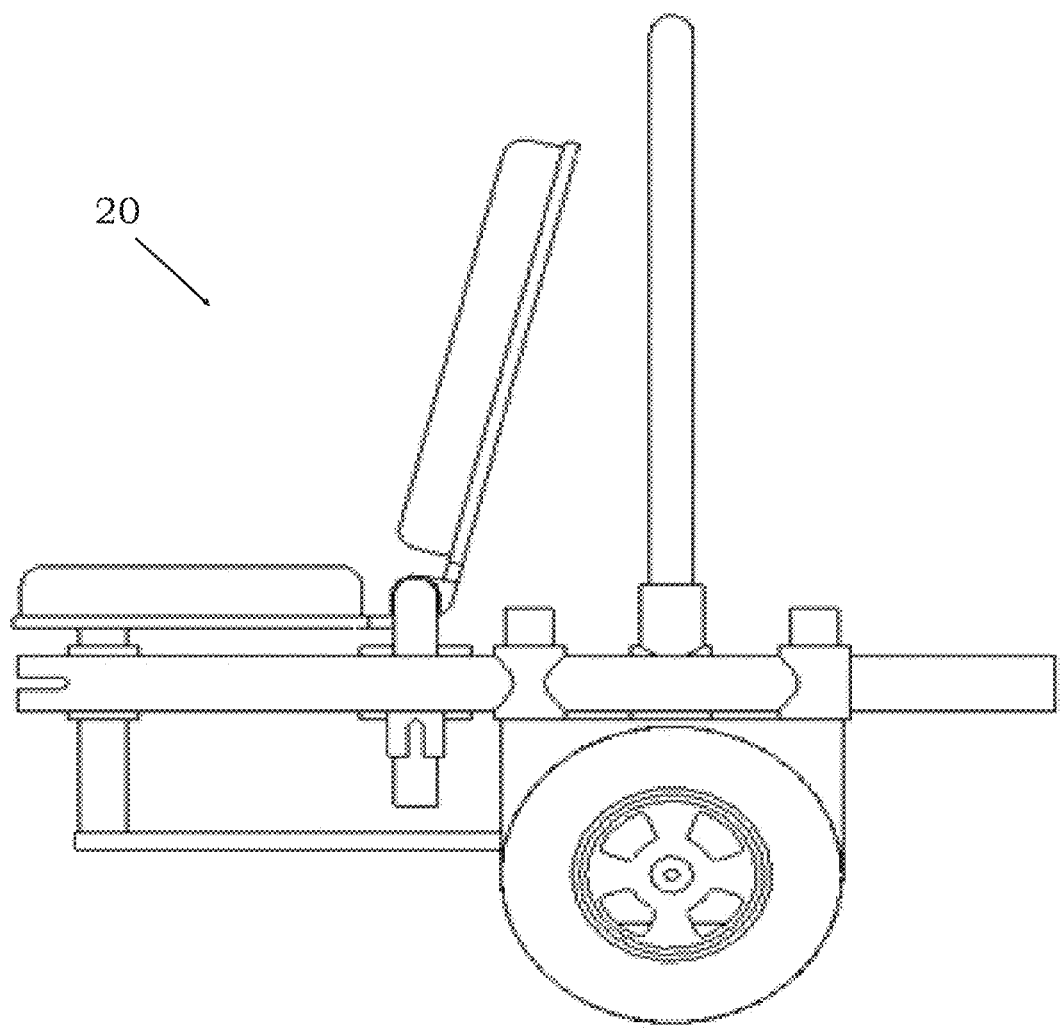
FIG. 9C is a perspective view of a portion of the medical mobility device showing the seat module in a first vertical position, according to an embodiment of the present disclosure.
Figure 9D:
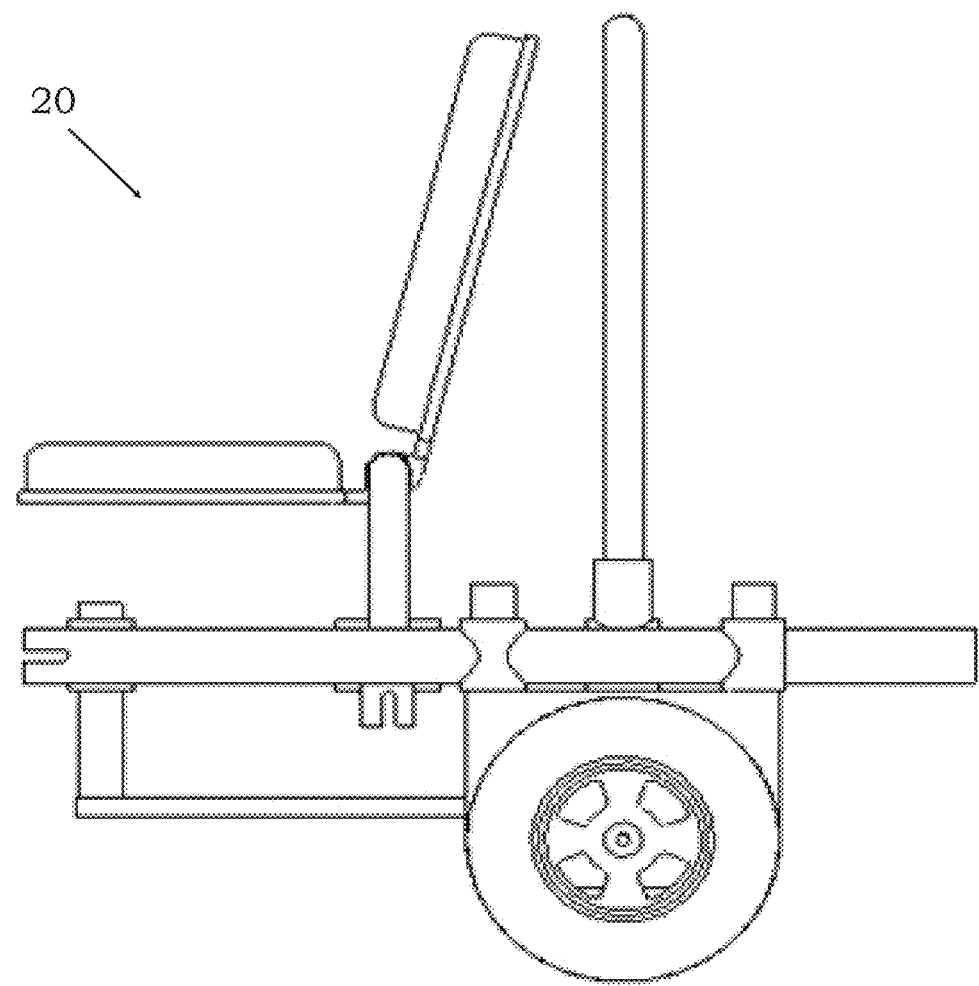
FIG. 9D is a perspective view of a portion of the medical mobility device showing the seat module in a second vertical position, according to an embodiment of the present disclosure.
Figure 9E:
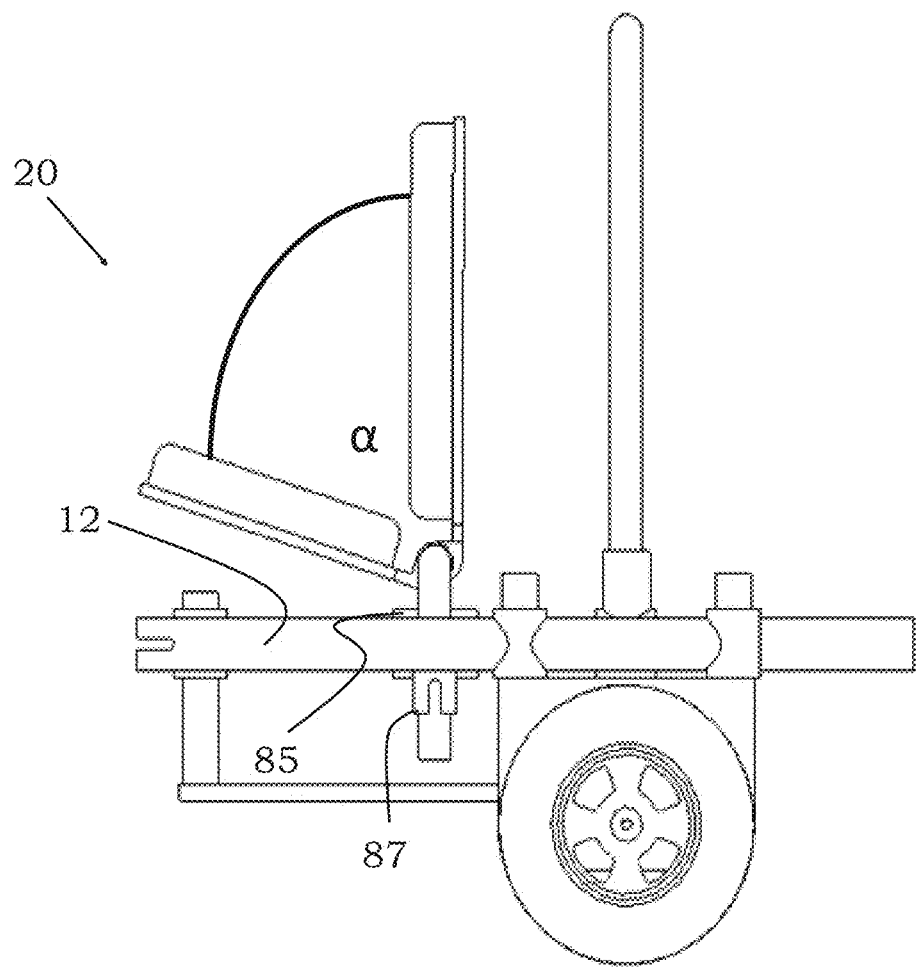
FIG. 9E is a side view of a portion of the medical mobility device showing the seat module in a first configuration, according to an embodiment of the present disclosure.
Figure 9F:
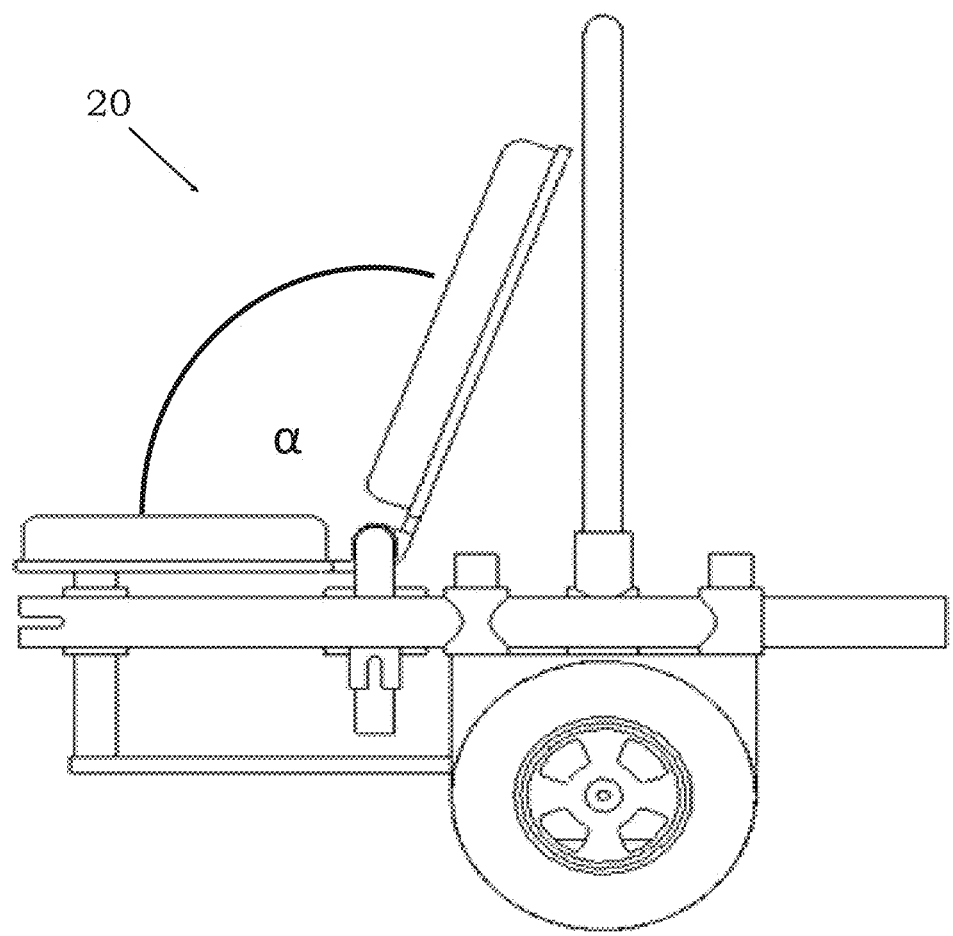
FIG. 9F is a side view of a portion of the medical mobility device showing the seat module in a second configuration, according to an embodiment of the present disclosure.
Figure 9G:
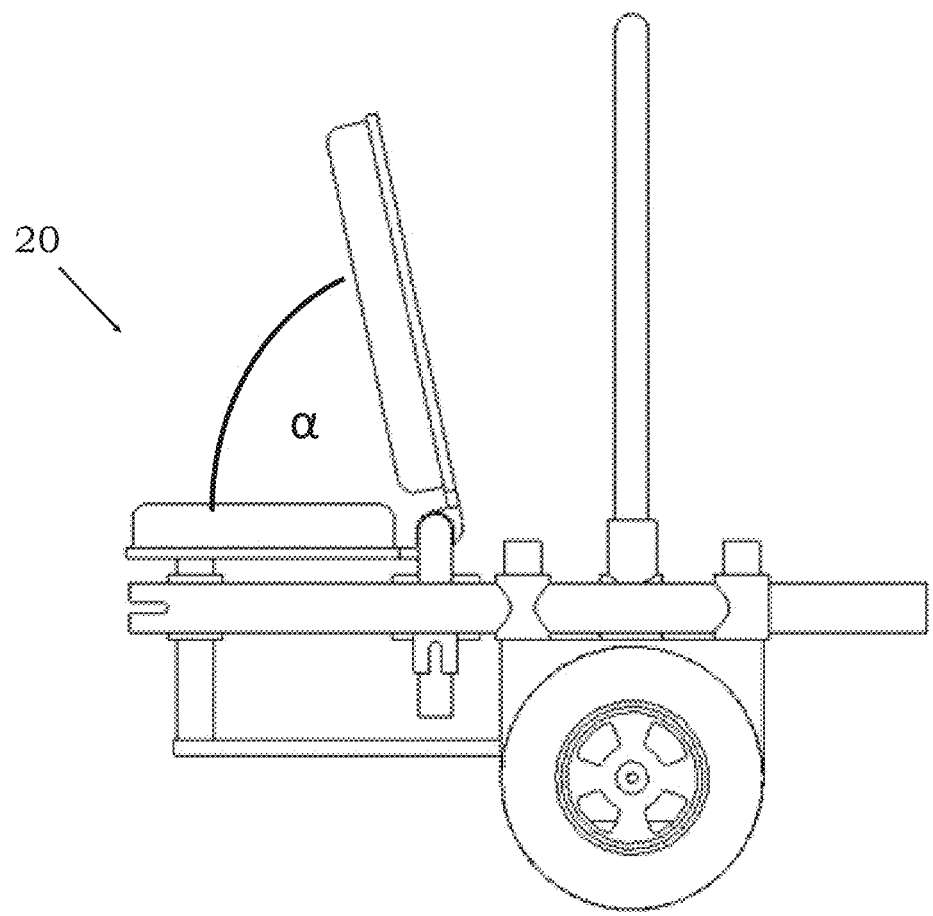
FIG. 9G is a side view of a portion of the medical mobility device showing the seat module in a third configuration, according to an embodiment of the present disclosure.
Figure 9H:
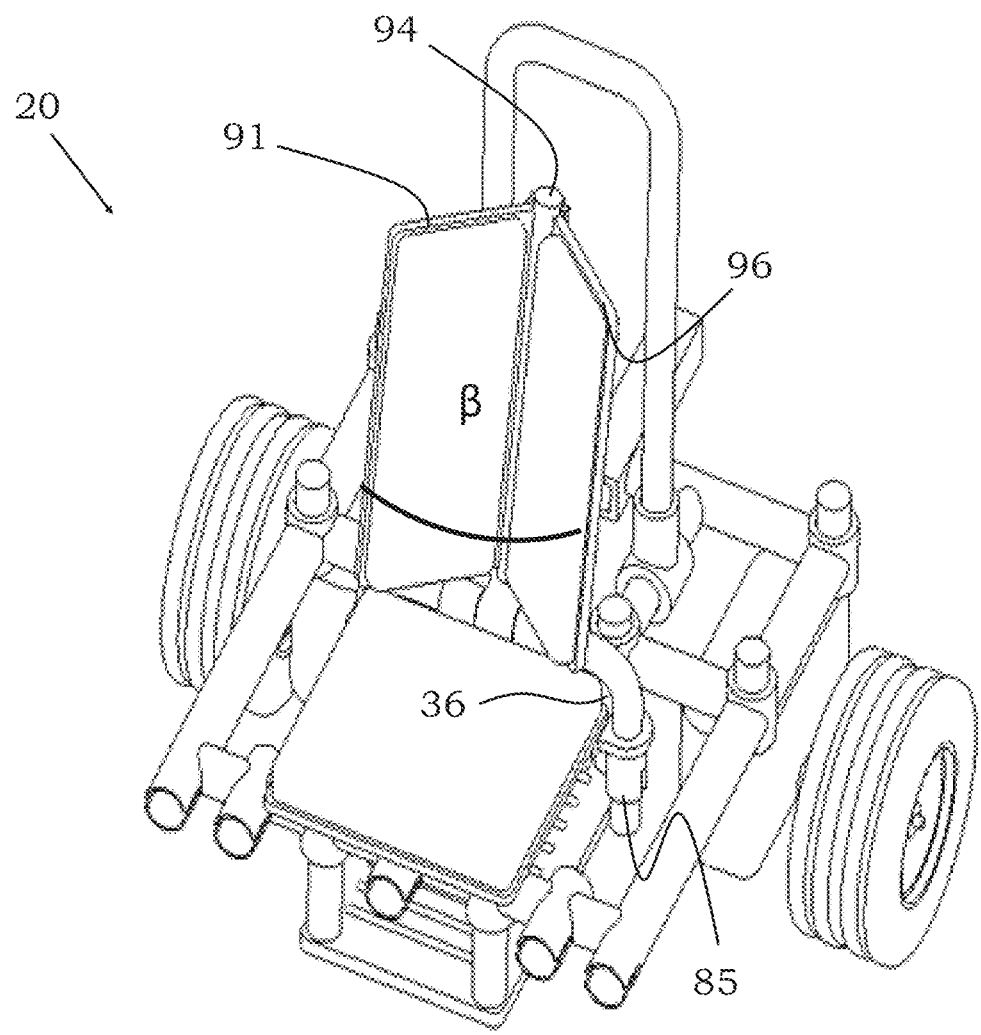
FIG. 9H depicts a perspective view of a portion of the medical mobility device, showing the second seat platform rotating about a seat extension member of the seat module, according to an embodiment of the present disclosure.

Referring to FIGS. 9A-9H, seating module 20 includes seat support bar 82, coupling member 84, and seat 86. Seat 86 is substantially rectangular and coupled to seat support bar 82 via first coupling member 84. Furthermore, second coupling member 85 secures seating module 20 with chassis 12. Specifically, seat support bar 82 is received within seat coupling aperture 87 of second coupling member 85. Moreover, coupling of seat support bar 82 within second coupling aperture 87 permits the adjustment of seat 86 in the x-direction with respect to chassis 12. Additionally, seat 86 is adjustable in the y-direction by slidably disposing second coupling member 85 along link 36. Seat 86 may be formed of one single body section or may include multiple body sections-such as first platform 88 and second platform 90. Each platform 88, 90 is configured to rotate about seat support bar 82, permitting the operator to adjust angle α independently. In an embodiment, the first 88 and second 90 platforms include cushion 92 that provides support and comfort to the operator during prolonged use. Cushion 92 may further include adjustable lumbar support and variable stiffness mechanisms. In an embodiment as depicted in FIG. 9H, seat support bar 82 includes seat support extension 94 extending away from seat support bar 82. Second platform 90 and third platform 96 are configured to rotate about seat support bar 82, allowing an operator to adjust angle β between the third platform 91 and fourth platforms 96.

Harness Module

Figure 10A:
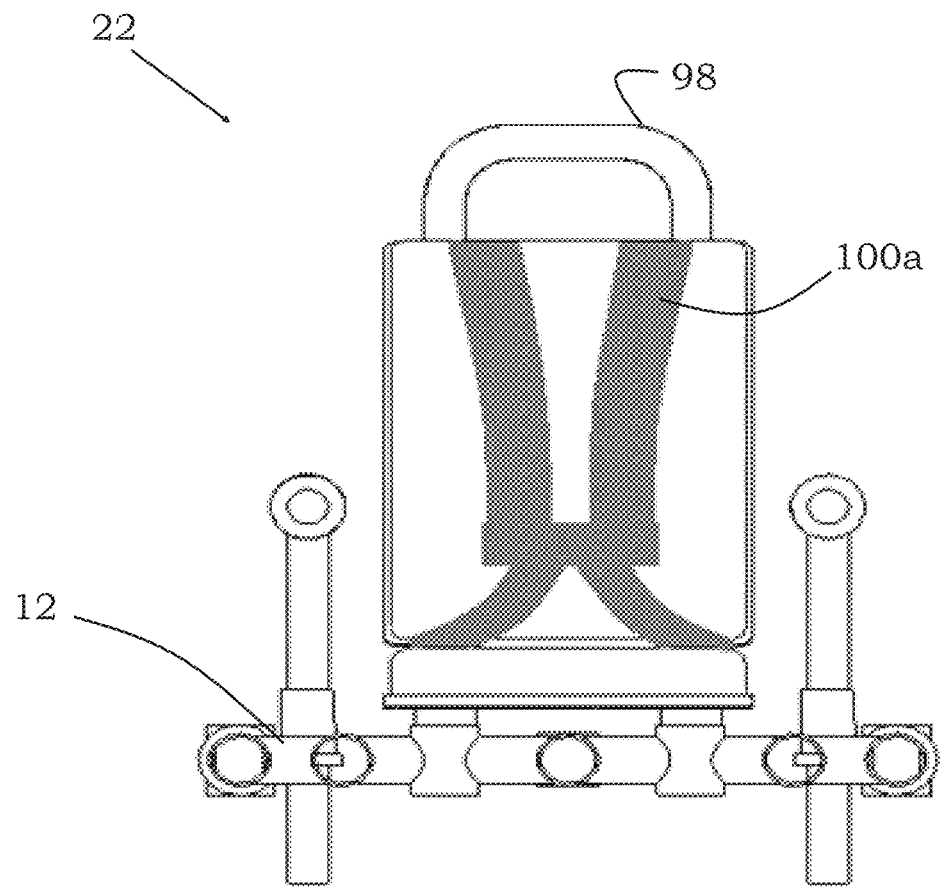
FIG. 10A is a front view of a portion of the medical mobility device depicting a harness bar module coupled to a harness in the form of a 4-point strap system, according to an embodiment of the present disclosure.
Figure 10B:
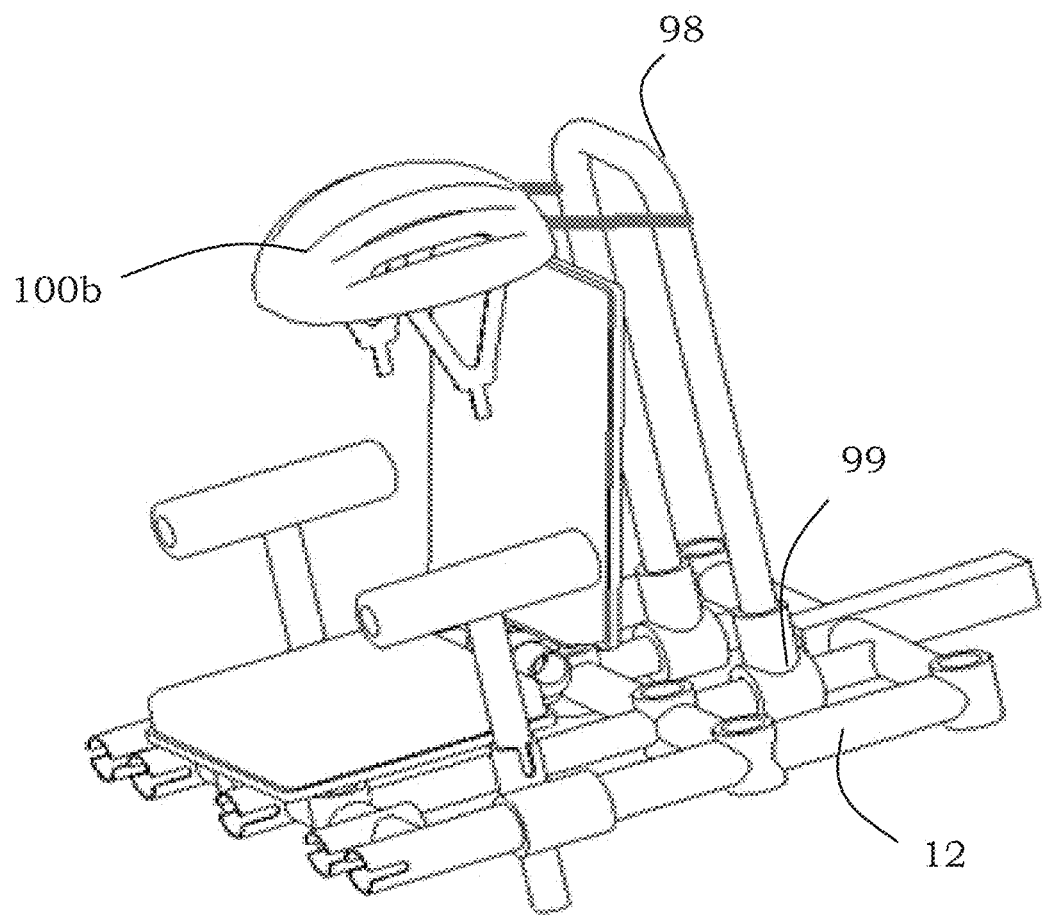
FIG. 10B is a perspective view of a portion of the medical mobility device depicting the harness bar module coupled to a harness in the form of a helmet to support and stabilize an operator's head, according to an embodiment of the present disclosure.
Figure 11A:
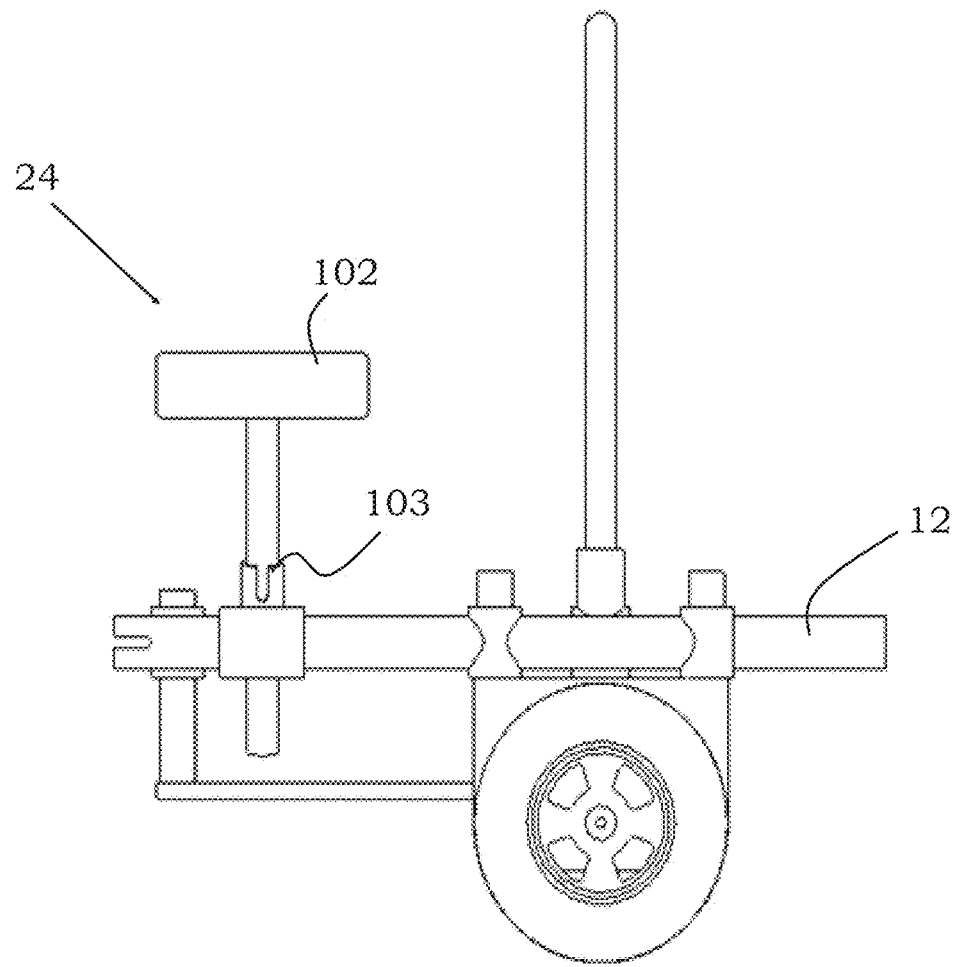
FIG. 11A is a side view of a portion of the medical mobility device depicting an armrest module in a first vertical configuration, according to an embodiment of the present disclosure.
Figure 11B:
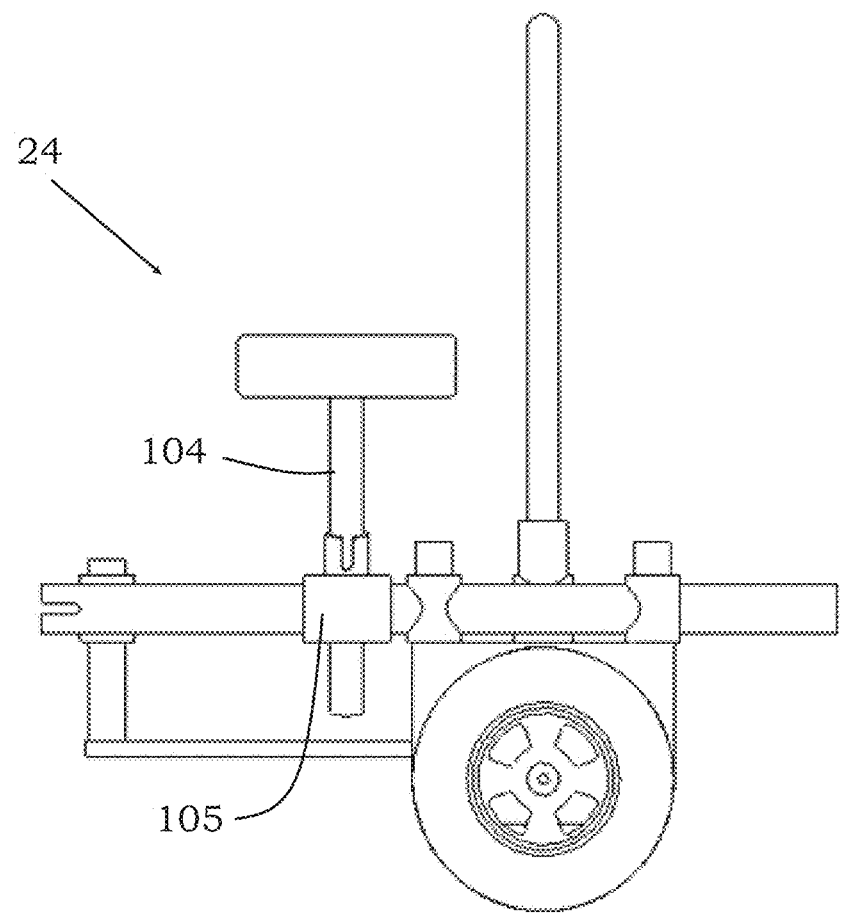
FIG. 11B is a side view of a portion of the medical mobility device depicting an armrest module in a second vertical configuration, according to an embodiment of the present disclosure.
Figure 11C:
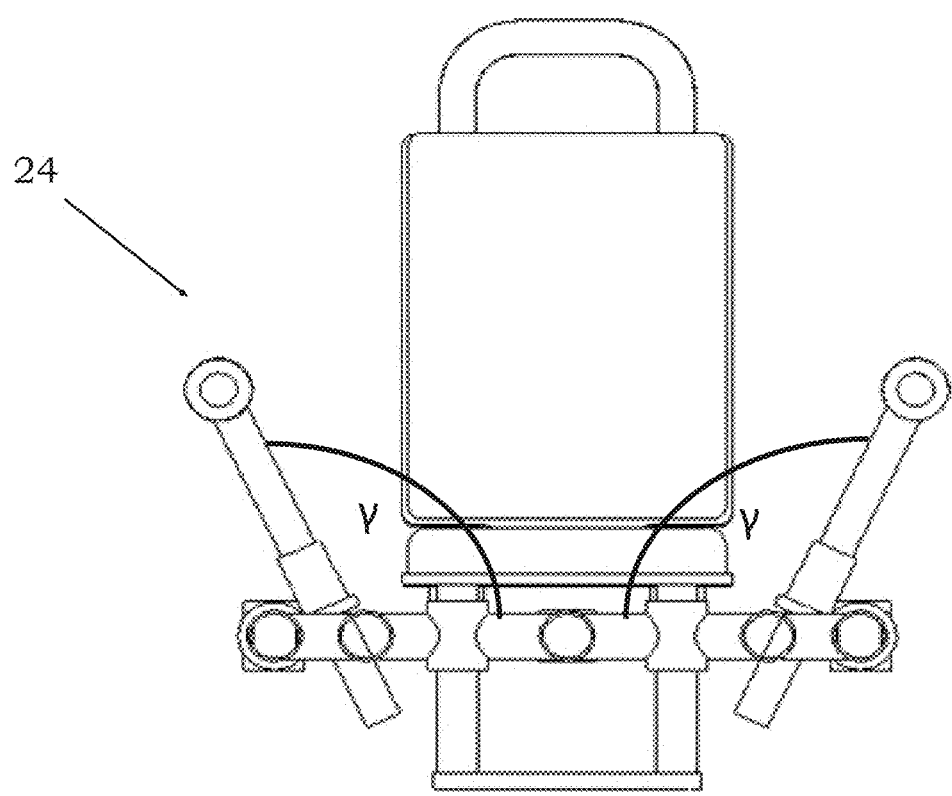
FIG. 11C is a front view of a portion of the medical mobility device depicting an armrest module, according to an embodiment of the present disclosure.
Figure 11D:
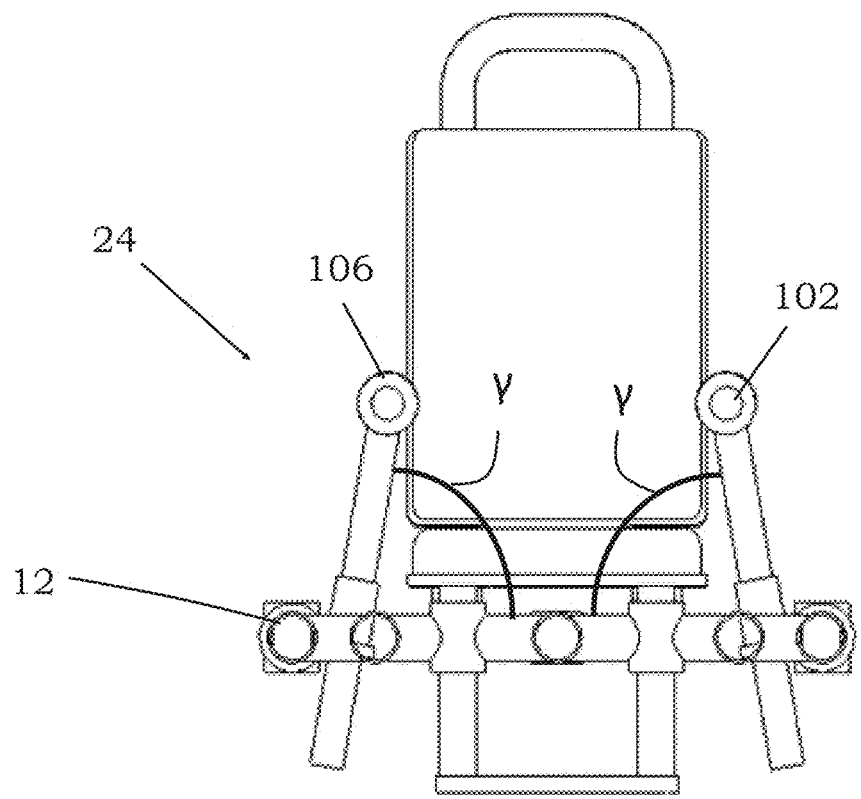
FIG. 11D is a front view of a portion of the medical mobility device depicting an armrest module, according to an embodiment of the present disclosure.
Figure 11E:
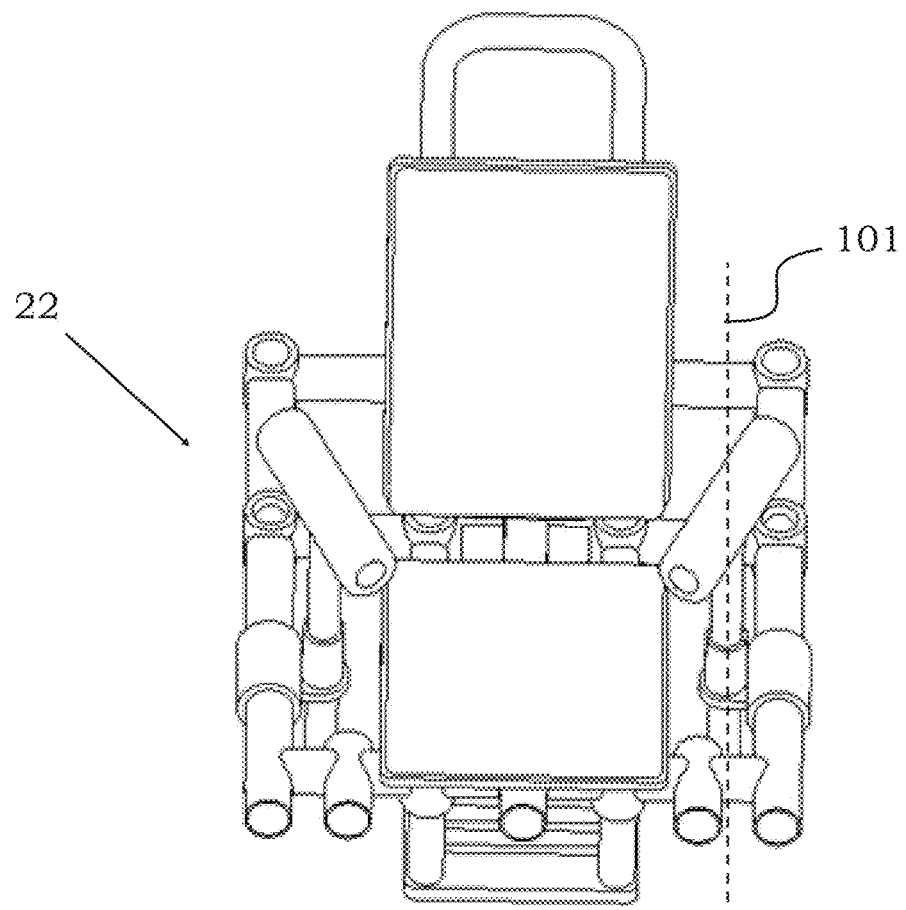
FIG. 11E is a perspective view of the armrest modules rotating about a longitudinal axis of the armrest extensions, according to an embodiment of the present disclosure.
Figure 11F:
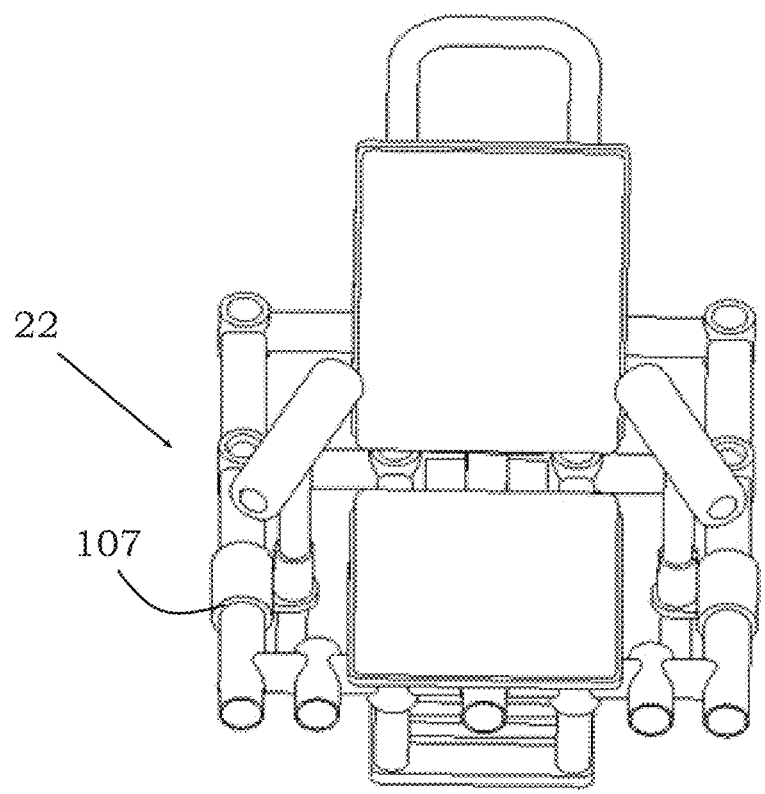
FIG. 11F is a perspective view of the armrest modules rotating about a longitudinal axis of the armrest extensions, according to an embodiment of the present disclosure.

Referring to FIG. 10A and FIG. 10B, harness module 22 includes harness support bar 98 having channel mounts 99 slidably disposed over links 36 of chassis 12. Harness module 22 is adjustable horizontally in the x-axis or vertically in the y-axis. Harness module 22 includes harness 100 coupled to at least a portion of the harness support bar 98 and secures an operator within medical mobility device 10. Harness 100 includes 4-point harness 100a, helmet 100b for head and heck stabilization, a lap bar, a 2-point harness, or other methods and devices used to secure an operator to medical mobility device 10.

Additionally, harnesses 100 are helpful for operators diagnosed with ALS and other degenerative neuromuscular diseases who may have trouble supporting their heads. Helmet 100b aids the operator in positioning their head in a natural and upright position. In an embodiment, one or more harnesses 100 are coupled to harness support bar 98.

Armrest Module

Referring to FIGS. 11A-11F, armrest module 24 includes armrest 102 disposed in an orthogonal relationship to armrest extension 104 and configured to rotate about armrest extension 104. Specifically, armrest 102 is rotatable about armrest axis 101 to angle armrest 102 toward or away from operator depending on the operator's specific needs. Armrest extension 104 is configured to be at least partially disposed within first channel 103 of armrest coupling 105. Moreover, vertical adjustment of armrest extension 104 within first channel 103 permits adjustment of armrest 102 proximally toward chassis 12 and distally away from chassis 12, such that a vertical position of armrest 102 can be customized to an individual operator's needs and desires.

Furthermore, armrest coupling 105 includes second channel 107 configured to be slidably disposed over link 32 thereby permitting the adjustment of armrest 102 horizontally with respect to chassis 12. In addition, second channel 107 of armrest coupling 105 is configured to rotate about link 32 to tilt armrest 102 away from or toward the operator, thereby increasing or decreasing angle γ respectfully.

To provide additional comfort and support, slip 106 is disposed over armrest 102 to provide padding for an operator to rest their arms during the operation of medical mobility device 10. Slip 106 can be formed having various diameters and stiffness depending on the operator's preference and needs. For example, larger diameter slips 106 can be used for smaller operators, while smaller diameter slips 106 can be used for larger operators. By adjusting the diameter of slip 106, correct positioning and comfort of the operator can be fine-tuned depending on the operator's requirements and preferences.

Leg Support Module

Figure 12A:
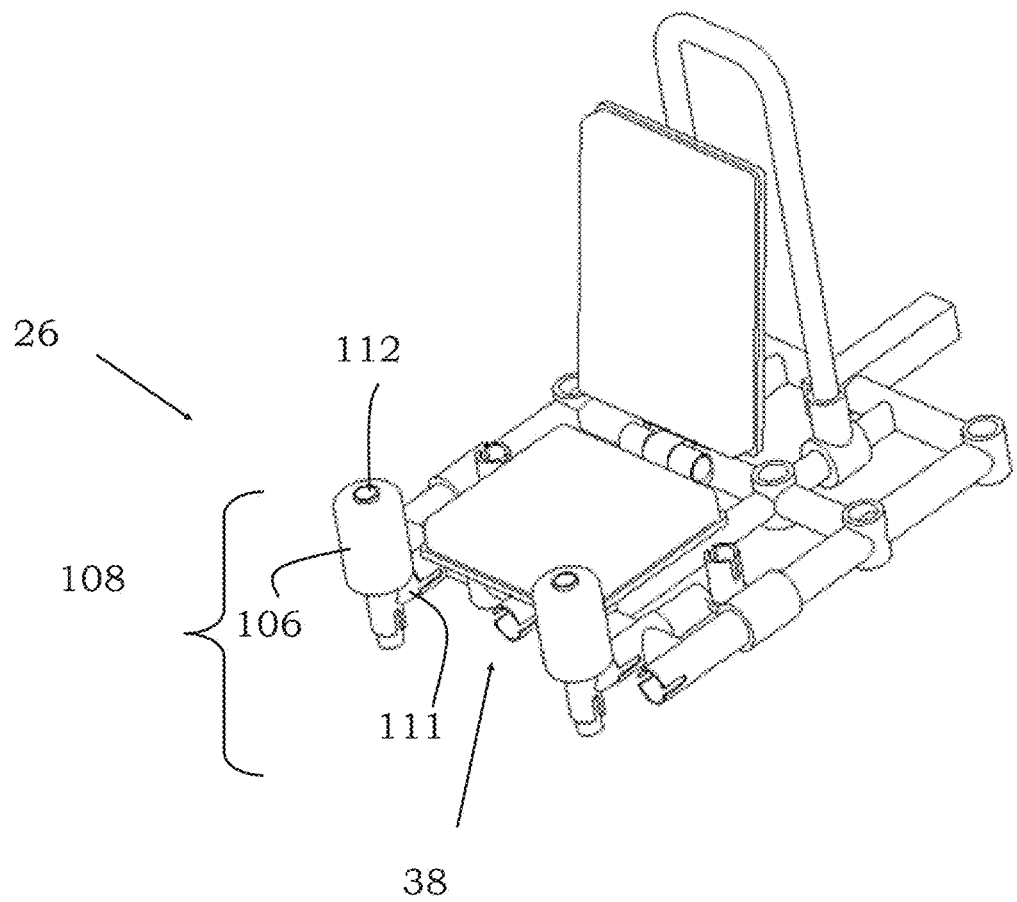
FIG. 12A is a perspective view of a pair of abduction bars coupled with the chassis, according to an embodiment of the present disclosure.
Figure 12B:
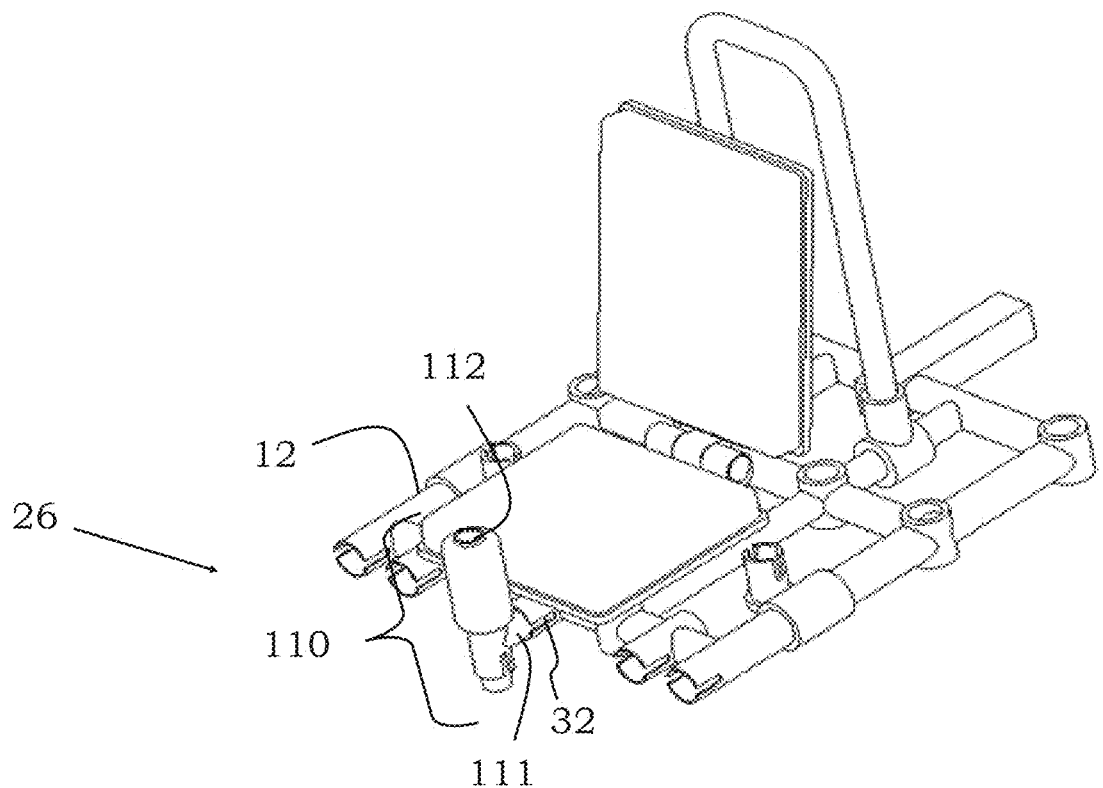
FIG. 12B is a perspective view depicting an adduction bar coupled to the chassis, according to an embodiment of the present disclosure.

Referring to FIG. 12A and FIG. 12B, leg support module 26 includes abduction bars 108 and/or adduction bars 110. Each of abduction bars 108 and adduction bar 110 includes terminal end 111 configured to be disposed within receiving aperture 38 of links 36. Slip 106 is disposed on origination end 112, such that slip 106 is configured to abut the legs of the operator. Abduction bars 108 are configured to stabilize the operator's legs and prevent the operator's legs from moving away from the midline of the operator's body. Similarly, adduction bar 110 is configured to stabilize the operator's legs and prevent the operator's legs from moving toward the midline of the body. Both abduction and adduction bars are adjustable horizontally and vertically to suit operator needs. Leg support modules 26 may not be required in embodiments in which operators have full functionality of their legs.

Footrest Module

Referring to FIGS. 13A-13H, footrest module 28 includes first footrest extension 114 positioned in an orthogonal relationship to second footrest extension 116. Second footrest extension 116 is spaced apart from and disposed parallel to links 36 of chassis 12. Adjustment of first footrest extension 114 within aperture of mounting point 32 provides for adjustment of footrest module 28 linearly along the y-axis in a vertical direction, such that second footrest extension 116 can be linearly translated toward and away from links 36 of chassis 12. In addition, disposing second footrest extension 116 through secondary mounting point 122 permits the coupling and adjustment of footrest module 28 linearly along an x-axis in a horizontal direction, such that second footrest extension 116 can linearly translated toward and away from first footrest extension 114.

Figure 13A:
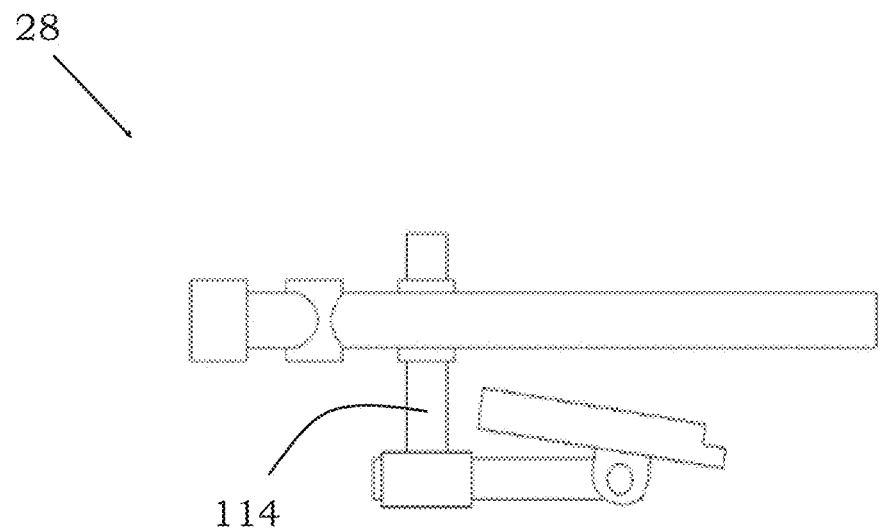
FIG. 13A is a side view of a footrest module, according to an embodiment of the present disclosure.
Figure 13B:
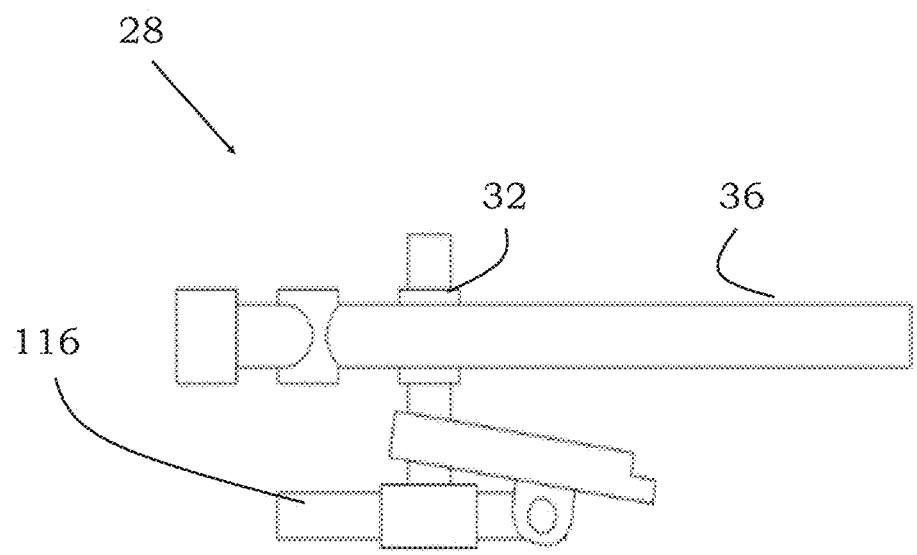
FIG. 13B is a side view of a footrest module, according to an embodiment of the present disclosure.
Figure 13C:
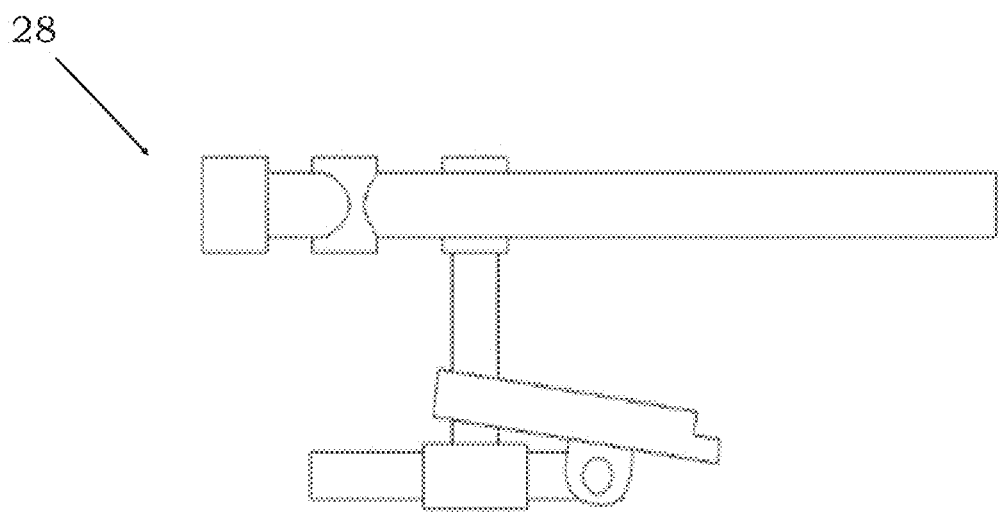
FIG. 13C is a side view of a footrest module, according to an embodiment of the present disclosure.
Figure 13D:
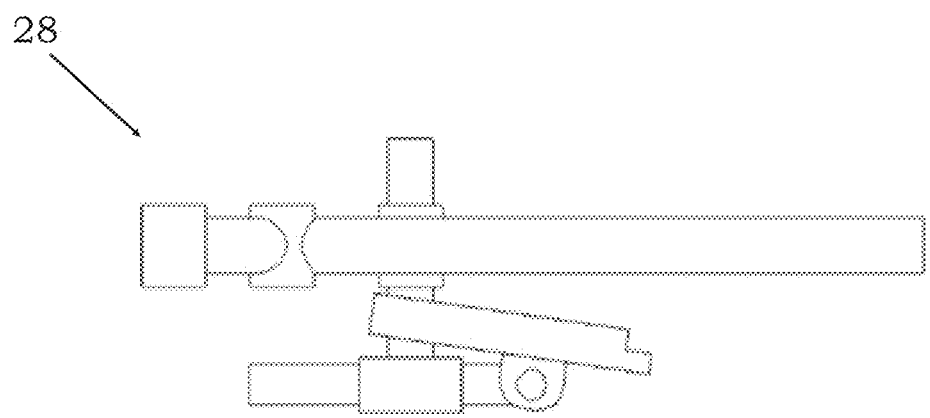
FIG. 13D is a side view of a footrest module, according to an embodiment of the present disclosure.
Figure 13E:
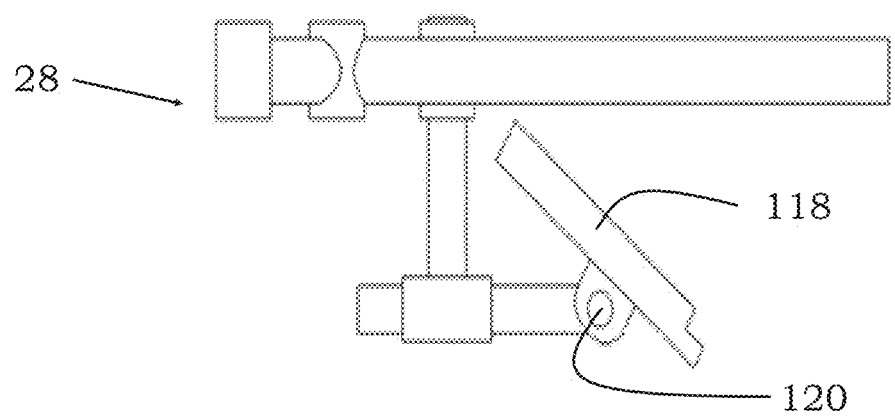
FIG. 13E is a side view of a footrest module, according to an embodiment of the present disclosure.
Figure 13F:
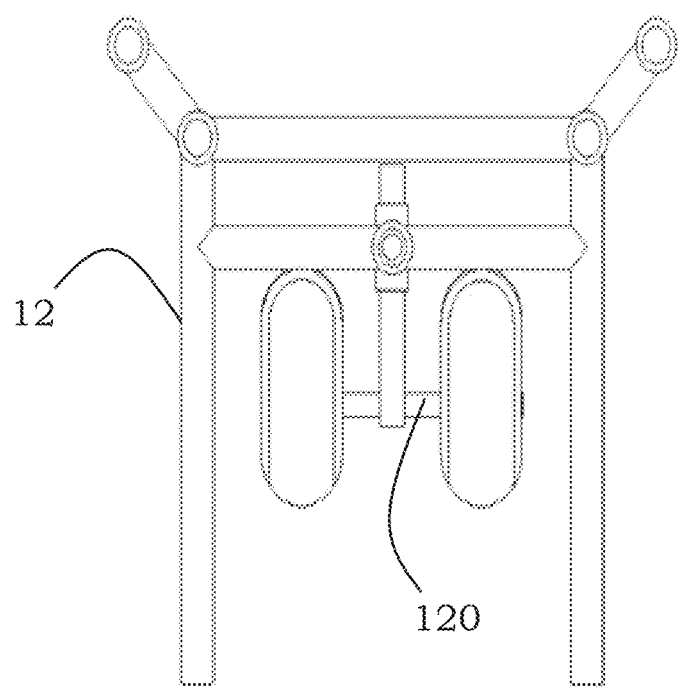
FIG. 13F is a top view of a footrest module, according to an embodiment of the present disclosure.
Figure 13G:
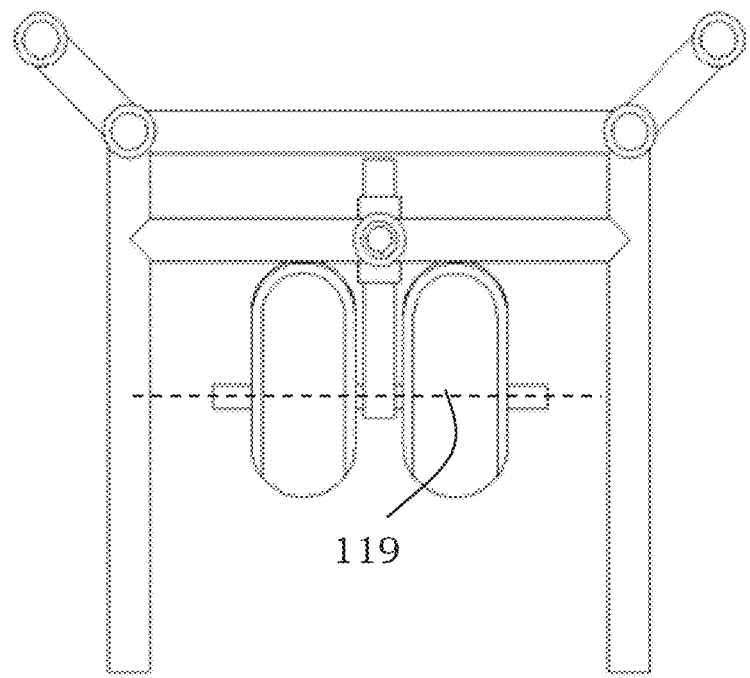
FIG. 13G is a top view of a footrest module, according to an embodiment of the present disclosure.
Figure 13H:
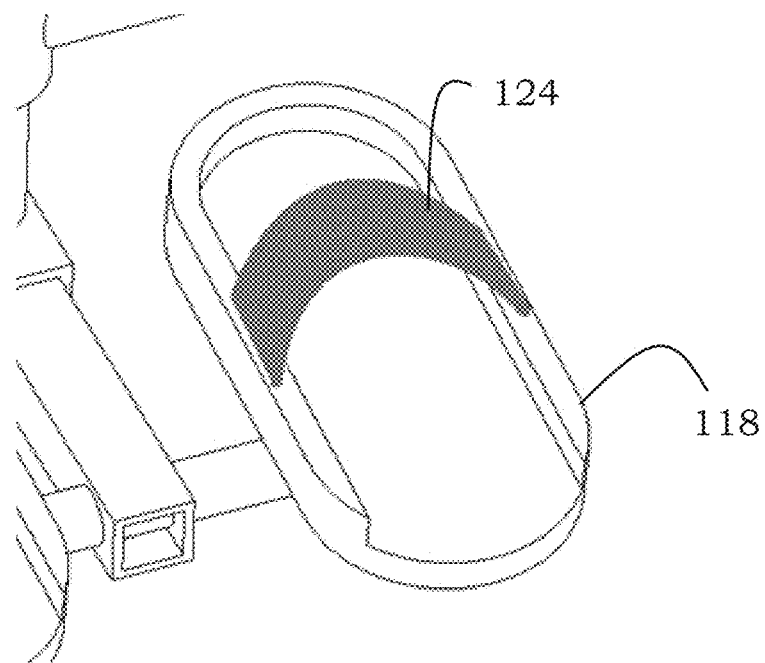
FIG. 13H is a perspective view of a portion of the footrest module, according to an embodiment of the present disclosure.
Figure 14A:
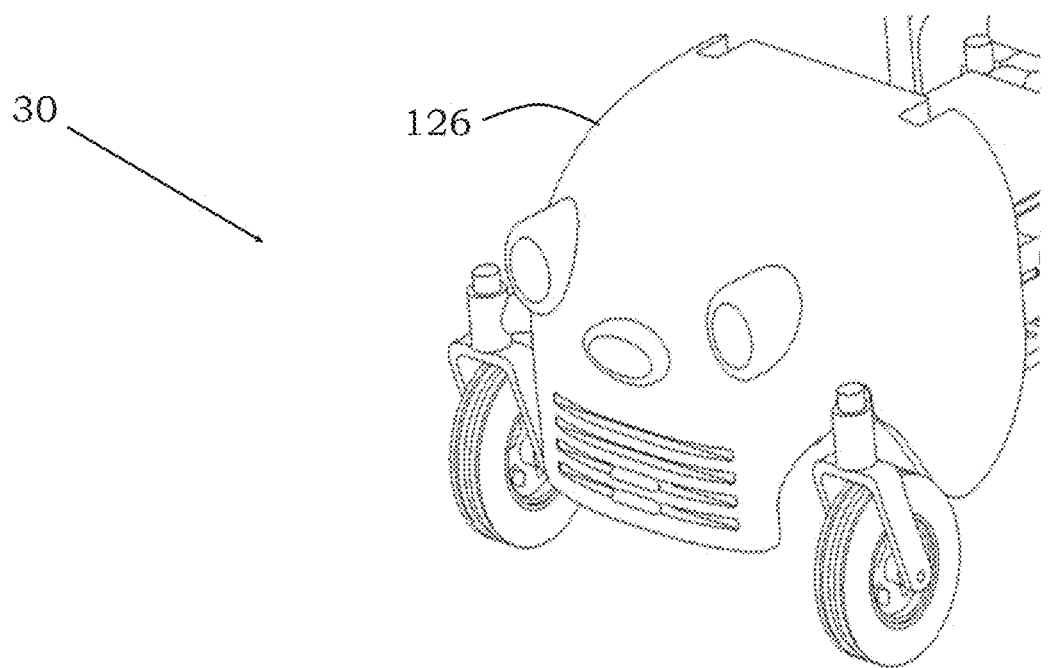
FIG. 14A is a perspective view of a portion of the medical mobility device showing the front body cover, according to an embodiment of the present disclosure.
Figure 14B:
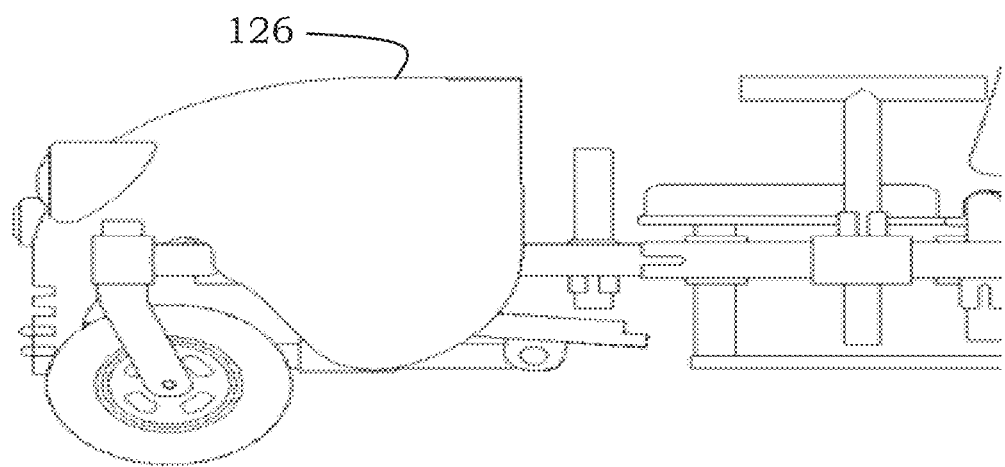
FIG. 14B is a side view of a portion of the medical mobility device showing the front body cover in the closed configuration, according to an embodiment of the present disclosure.
Figure 14C:
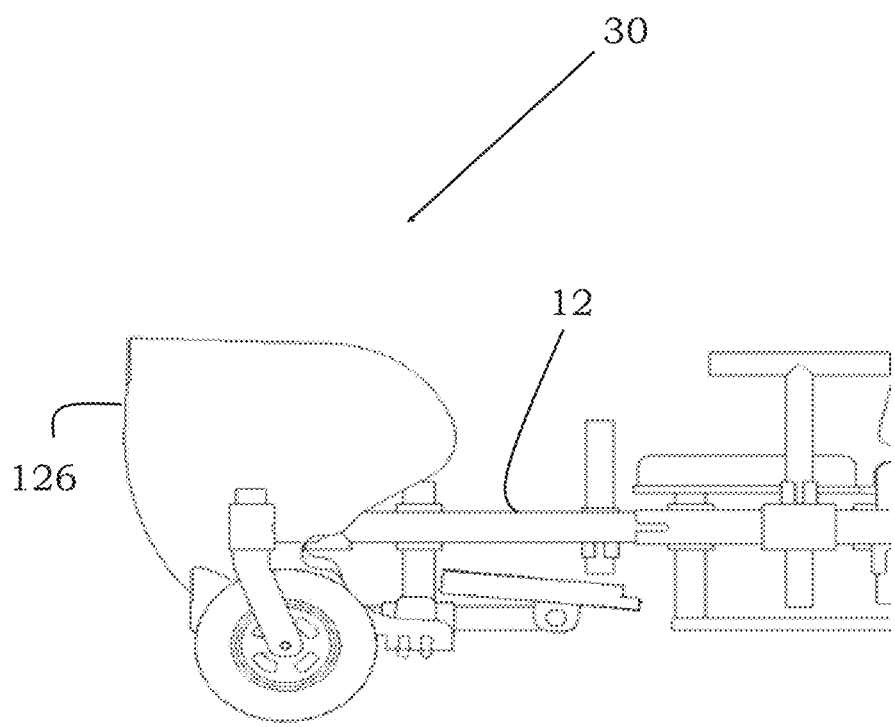
FIG. 14C is a side view of a portion of the medical mobility device showing the front body cover in the open configuration, according to an embodiment of the present disclosure.
Figure 14D:
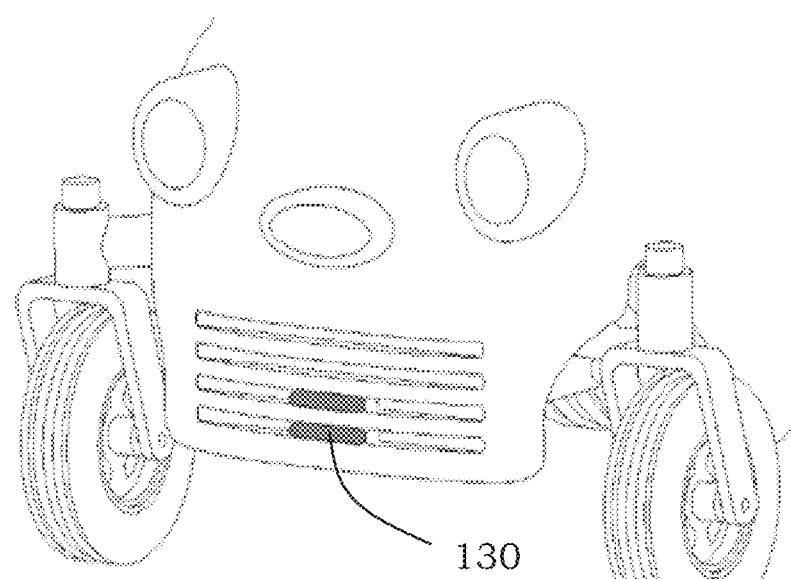
FIG. 14D is a perspective view of the front body cover showing the in-line sensor coupled with the front body cover, according to an embodiment of the present disclosure.
Figure 14E:
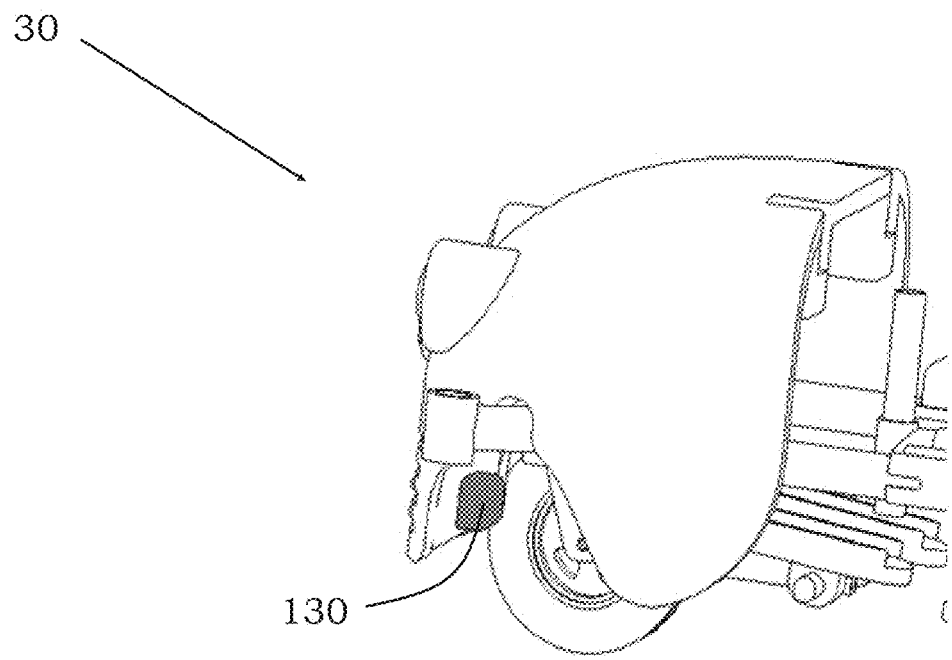
FIG. 14E is a perspective view of the front body cover showing the in-line sensor coupled with the front body cover, according to an embodiment of the present disclosure.
Figure 14F:
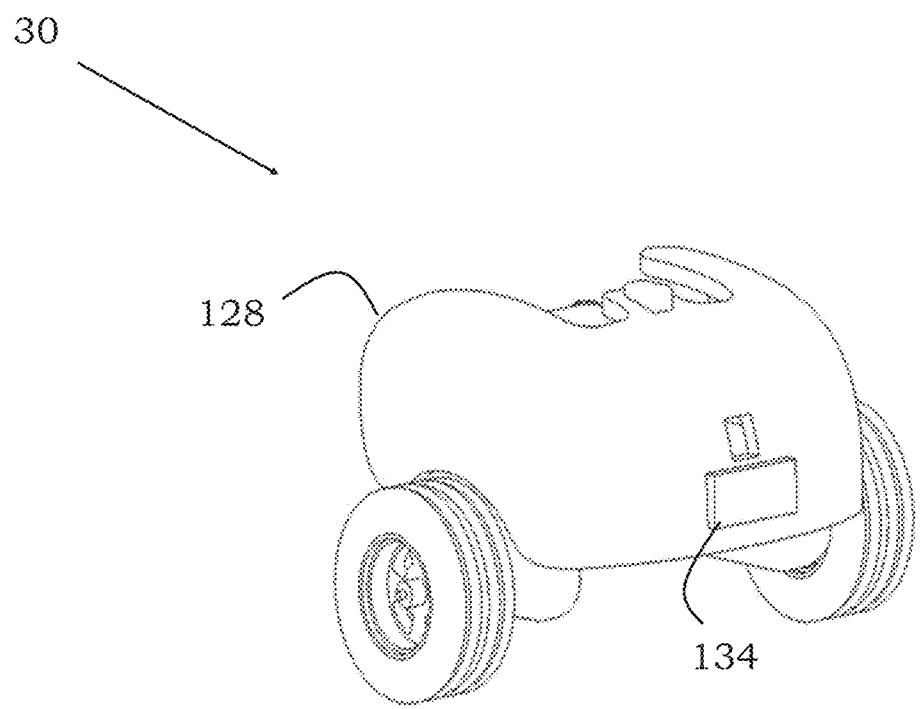
FIG. 14F is a perspective view of the rear body cover of the medical mobility device, according to an embodiment of the present disclosure.
Figure 14G:
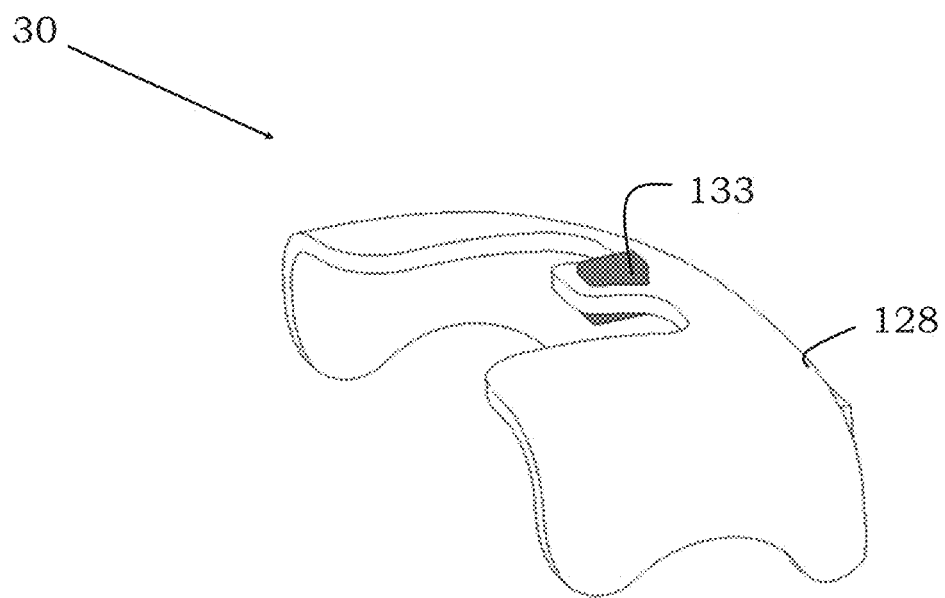
FIG. 14G is a perspective view of the rear body cover with navigation system and electronics disposed within the medical mobility device's rear body cover, according to an embodiment of the present disclosure.

As shown in particular in FIG. 13E, footrest plates 118 are configured to support one or more feet (i.e., distal part of the leg) of an operator. A single footrest plate 118 may be provided in an embodiment that supports both of the operator's feet. In an embodiment, as depicted in FIG. 13H, footrest plate 118 may include strap 124 for securing an operator's feet to footrest module 28. Footrest plates 118 are configured to rotate about footrest axis 119 of third footrest extension 120 and adjust the angle to which the user's feet are positioned with respect to the operator.

Body Module

Referring to FIGS. 14A-14G, body module 30 includes front body component 126, and rear body component 128 mounted onto chassis 12. Body modules 30 protect the operator from external objects while operating medical mobility device 10. Front body component 126 is configured to rotate about links 36 of chassis 12 to allow for a more accessible operator entrance and exit from medical mobility device 10. In some embodiments, front body component 126 is configured to contain in-line follow sensors and electronics 130. Rear body component 128 is mounted to chassis 12 and protects drive modules 16 and associated electronics 130. In an embodiment, rear body component 128 contains indoor navigation system sensors 133. Rear plate holder 134 may also be present to allow the personalization of medical mobility device 10 and is configured to receive an indicia portion. In an embodiment, body module 30 is configured to receive one or more lights.

In use, the medical mobility device is configured to adjust with the operator's evolving medical needs by providing for the adjustment of one or more of the modules. Specifically, the medical mobility device's chassis is configured to support each of the modules through a series of links and mounting points that provide for adjustment of the modules with respect to the chassis. As the needs and preference of operators change, the modules can be adjusted as well, thereby ensuring that the operator can comfortably and safely interact with the medical mobility device. Such adjustments increase economic efficiencies related to the operation of a medical mobility device, since the modular and adjustable nature of the device reduces the need to replace an existing device that has been physically outgrown. Moreover, using the same medical mobility device over time imparts a high level of comfort on the operator. Such a high comfort level is especially important for operators suffering from mental disabilities, for whom familiarity can be crucial. Accordingly, the medical mobility device provides for an efficiently adjustable device that can accommodate a plurality of needs and requirements of an operator, including flexible adjustments based on physical changes of the operator, to reduce the requirement to replace the device upon the operator's growth or disease progression.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

It is also to be understood that the following claims are intended to cover all of the generic and specific features of the invention herein described, and all statements of the scope of the invention which, as a matter of language, might be said to fall therebetween.

What is claimed is:

1. A medical mobility device, the medical mobility device comprising:
   a chassis having a first end opposite a second end, the chassis comprising a plurality of mounting points;
   a frame, the frame comprising a frame extension removably received within a first mounting point of the plurality of mounting points, the first mounting point disposed at the first end of the chassis, the first mounting point being a first chassis aperture; and
   wherein an overall length of the medical mobility device is adjustable by a translation of the frame extension within the first chassis aperture.

2. The medical mobility device of claim 1, further comprising a drive module comprising a drive shaft having a first end and a second end, whereby the first end of the drive shaft is in mechanical communication with a drive wheel, the second end of the drive shaft is in mechanical communication with a motor, or both.

3. The medical mobility device of claim 2, wherein the motor comprises a power supply, the power supply being a battery configured to supply an amount of electrical energy to the motor, such that the motor converts the electrical energy to mechanical energy, thereby propelling the medical mobility device along a surface.

4. The medical mobility device of claim 3, wherein the drive module further comprises a drive module extension received within a second mounting point of the plurality of mounting points, the second mounting point disposed in an underlying relation at the second end of the chassis, the second mounting point being a second chassis aperture, wherein the motor is adapted to impart axial rotation onto the drive wheel via the rotation of the drive shaft, such that the medical mobility device is translatable along a surface when the drive shaft is rotated.

5. The medical mobility device of claim 2, further comprising:
   a second drive module spaced apart from the first drive module, the second drive module disposed at the second end of the chassis and in an underlying relation to the chassis, including a second drive shaft having a first end and a second end, the first end of the second drive shaft is in mechanical communication with a second drive wheel and the second end of the drive shaft is in mechanical communication with a second drive motor; and
   wherein the first drive module and the second drive module share a common central longitudinal axis and are configured to operate independently from one another, such that the medical mobility device has a zero-turn radius.

6. The medical mobility device of claim 2, further comprising:
   a hitch coupled at the second end of the chassis, such that the hitch is disposed between the second end of the chassis and the drive module; and
   an attachment slidably received within the hitch, the attachment configured to secure a medical oxygen tank to the chassis, the medical oxygen tank adapted to supply an amount of oxygen to an operator during operation of the medical mobility device.

7. The medical mobility device of claim 1, further comprising:
   a leg support module including an adduction bar having an origination end opposite a terminal end, the terminal end configured to be secured within a fourth mounting point of the plurality of mounting points, the fourth mounting point extending upwardly from an upper surface of the chassis, the fourth mounting point being a fourth chassis aperture; and
   wherein the origination end of the adduction bar is adapted to be disposed between the operator's legs, such that the adduction bar prevents the operator's legs from being disposed toward a central longitudinal axis of the adduction bar.

8. The medical mobility device of claim 1, further comprising:
   a leg support module including a first abduction bar and a second abduction bar, each of the first and the second abduction bars having an origination end opposite a terminal end, each terminal end configured to be secured within a fifth and a sixth mounting points respectively, each of the fifth and sixth mounting points extending upwardly from an upper surface of the chassis, the fifth mounting point being a fifth chassis aperture and the sixth mounting point being a sixth chassis aperture; and
   wherein each of the first and the second abduction bars is adapted to be disposed between a side of the leg support module and the operator, such that each of the first and the second abduction bars is adapted to prevent the operator's legs from reaching the side of the leg support module.

9. The medical mobility device of claim 1, further comprising:
   a seating module including a support bar having a first end opposite a second end, the first end of the support bar coupled to a seventh mounting point of the plurality of mounting points, the seventh mounting point residing above the power module, the seventh mounting point being an outer surface of a first link of the chassis, and the second end of the support bar coupled an eighth mounting point of the plurality of mounting points, the eighth mounting point residing above the power module, the eighth mounting point being an outer surface of a second link of the chassis, wherein the first link is different than the second link; and
   the seating module further comprising a first platform and a second platform, each of the first and the second platforms coupled to a portion of the support bar and configured to rotate about the support bar, thereby permitting the operator to adjust an angle α formed between each of the first and the second platforms.

10. A medical mobility device for use by an operator having a developmental disability, a physical disability, or both, the medical mobility device comprising:
   a chassis having a first end opposite a second end, the chassis comprising a plurality of mounting points;
   a frame, the frame comprising a frame extension in mechanical communication with the chassis, wherein the frame extension is at least partially slidably received within a first mounting point of the plurality of mounting points, whereby an overall length of the medical mobility device is adjustable by a translation of the frame extension within the first mounting point; and
   a drive shaft, the drive shaft comprising a first end and a second end, wherein the first end of the drive shaft is in mechanical communication with a drive wheel, the second end of the drive shaft is in mechanical communication with a motor, or both.

11. The medical mobility device of claim 10, wherein the motor is adapted to impart axial rotation onto the drive wheel via rotation of the drive shaft.

12. The medical mobility device of claim 10, further comprising:
   a harness support bar in mechanical communication with the chassis, the harness support bar extending upwardly from the chassis from a proximal end to a distal end;
   a harness coupled to a portion of the harness support bar between the proximal end and the distal end of the harness support bar; and
   a channel mount in mechanical communication with a third mounting point of the chassis, the third mounting point of the chassis being an outer surface of a link, wherein the channel mount is configured to be slidably disposed over the outer surface of the link, thereby coupling the harness module to the chassis, such that the harness module is translatable along the outer surface of the link.

13. The medical mobility device of claim 10, further comprising:
   a seating support bar having a first end opposite a second end, the first end of the seating support bar coupled to a fourth mounting point of the plurality of mounting points, the fourth mounting point being an outer surface of a second link of the chassis and the second end of the seating support bar coupled to a fifth mounting point, the fifth mounting point being an outer surface of a second link of the chassis, wherein the second link is different than the third link; and
   a first platform being coupled to a portion of the seating support bar and configured to rotate about the seating support bar.

14. The medical mobility device of claim 13, further comprising:
   a seat support extension having a first end opposite a second end, wherein the first end is coupled to the sixth mounting point of the plurality of mounting points, the sixth mounting point residing between the front end of the chassis and the second end of the chassis, the sixth mounting point being an outer surface of a fourth link of the chassis, the fourth link being different from each of the first and the second links; and
   a first angled platform coupled to the seat support extension and a second angled platform coupled to the seat support extension, wherein each of the first and the second angled platforms are configured to rotate about the seat support extension, thereby permitting the operator to adjust an angle R formed between each of the first and second angled platforms.

15. The medical mobility device of claim 10, wherein the chassis further includes:
   a hitch coupled at the second end of the chassis; and
   an attachment slidably received within the hitch, the attachment configured to secure a medical oxygen tank to the chassis, the medical supply tank adapted to supply an amount of oxygen to the operator during operation of the medical mobility device.

16. The medical mobility device of claim 10, further comprising a power module disposed between the first end and the second end of the chassis and in an underlying relation to the chassis.

17. The medical mobility device of claim 16, wherein the power module further comprises:
   a support having a first end opposite a second end, the second end received within a third mounting point of the plurality of mounting points, the third mounting point extending from a bottom surface of the chassis, the third mounting point being a third chassis aperture;
   a base perpendicularly secured to the first end of the support, such that the base resides within a third plane that is parallel to a first plane of the chassis; and
   a power supply secured within the power module, the power supply residing between the base and the chassis, wherein the power supply is in electrical communication with and is configured to supply an amount of power to the motor.

18. The medical mobility device of claim 17, wherein the power supply is a battery configured to supply an amount of electrical energy to the motor, such that the motor converts the electrical energy to mechanical energy, thereby propelling the medical mobility device along the surface.

19. The medical mobility device of claim 17, wherein the power module further comprises a plurality of removable sides coupled to the support of the power module, each of the plurality of removable sides spanning from the first end to the second end thereof, wherein the plurality of removable sides prevents foreign objects from damaging the power supply housed within the power module during operation of the medical mobility device.

20. A method of producing a medical mobility device, the method comprising:
   providing a chassis having a first end opposite a second end, the chassis comprising a plurality of mounting points;
   securing a frame to the chassis, wherein the frame comprising a frame extension in mechanical communication with the chassis, wherein the frame extension is at least partially slidably received within a first mounting point of the plurality of mounting points, whereby an overall length of the medical mobility device is adjustable by a translation of the frame extension within the first mounting point; and
   attaching a drive shaft to the chassis, wherein the drive shaft comprises a first end and a second end, the first end of the drive shaft being in mechanical communication with a drive wheel, the second end of the drive shaft being in mechanical communication with a motor, or both.

* * * * *